US012004860B2

(12) United States Patent
Klein et al.

(10) Patent No.: US 12,004,860 B2
(45) Date of Patent: Jun. 11, 2024

(54) CARDIAC FUNCTION ASSESSMENT USING MACHINE-LEARNING ALGORITHMS

(71) Applicant: SIEMENS HEALTHINEERS AG, Forchheim (DE)

(72) Inventors: Paul Klein, Princeton, NJ (US); Ingo Schmuecking, Yardley, PA (US); Costin Florian Ciusdel, Azuga (RO); Lucian Mihai Itu, Brasov (RO); Tiziano Passerini, Plainsboro, NJ (US); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 404 days.

(21) Appl. No.: 17/305,391

(22) Filed: Jul. 7, 2021

(65) Prior Publication Data

US 2022/0031218 A1    Feb. 3, 2022

(30) Foreign Application Priority Data

Jul. 31, 2020 (DE) .......................... 102020209696.1
Jul. 31, 2020 (EP) .................................... 20465550

(51) Int. Cl.
*A61B 5/308* (2021.01)
*A61B 5/00* (2006.01)
*A61B 5/026* (2006.01)

(52) U.S. Cl.
CPC .............. *A61B 5/308* (2021.01); *A61B 5/026* (2013.01); *A61B 5/7267* (2013.01)

(58) Field of Classification Search
CPC ....... A61B 5/308; A61B 5/026; A61B 5/7267; A61B 5/02028; A61B 5/7264; G16H 30/40; G16H 50/20; G16H 50/30; G16H 50/50
See application file for complete search history.

(56) References Cited

U.S. PATENT DOCUMENTS 10,470,677 B2 * 11/2019 Cadieu ................... A61B 5/029
2009/0093707 A1 *  4/2009 Maier .................. A61B 5/7257
                                                        600/410

(Continued)

FOREIGN PATENT DOCUMENTS

DE     112018004546 T5    6/2020
WO     WO2019178404 A1    9/2019

OTHER PUBLICATIONS

American Heart Association Writing Group on Myocardial Segmentation and Registration for Cardiac Imaging:, et al. "Standardized myocardial segmentation and nomenclature for tomographic imaging of the heart: a statement for healthcare professionals from the Cardiac Imaging Committee of the Council on Clinical Cardiology of the American Heart Association." Circulation 105.4 (2002): 539-542.

(Continued)

*Primary Examiner* — Dhaval V Patel

(57) ABSTRACT

A method includes processing at least one input dataset (using a multi-level processing algorithm, one or more of the at least one input dataset comprising imaging data of an echocardiography of a cardiovascular system of a patient. The multi-level processing algorithm comprises a multi-task level and a consolidation-task level. An input of the consolidation-task level is coupled to an output of the multi-task level. The multi-task level is configured to determine multiple diagnostic metrics of the cardiovascular system based on the at least one input dataset. The consolidation-task level is configured to determine a fitness of the cardiovascular system of the patient.

22 Claims, 13 Drawing Sheets

(56) References Cited

U.S. PATENT DOCUMENTS

| | | | |
|---|---|---|---|
| 2016/0106321 A1 | 4/2016 | Sharma et al. | |
| 2017/0109881 A1 | 4/2017 | Avendi et al. | |
| 2018/0157743 A1* | 6/2018 | Hori | G06F 16/35 |
| 2019/0139641 A1* | 5/2019 | Itu | G06N 3/045 |
| 2019/0371450 A1 | 12/2019 | Lou et al. | |

OTHER PUBLICATIONS

Armstrong, William F., and William A. Zoghbi. "Stress echocardiography: current methodology and clinical applications." Journal of the American college of cardiology 45.11 (2005): 1739-1747.

Heijenbrok-Kal, Majanka H., Kirsten E. Fleischmann, and MG Myriam Hunink. "Stress echocardiography, stress single-photon-emission computed tomography and electron beam computed tomography for the assessment of coronary artery disease: a meta-analysis of diagnostic performance." American heart journal 154.3 (2007): 415-423.

Heimdal, Andreas, et al. "Real-time strain rate imaging of the left ventricle by ultrasound." Journal of the American Society of Echocardiography 11.11 (1998): 1013-1019.

Leitman, Marina, et al. "Two-dimensional strain—a novel software for real-time quantitative echocardiographic assessment of myocardial function." Journal of the American Society of Echocardiography 17.10 (2004): 1021-1029.

Pellikka, Patricia A., et al. "Guidelines for performance, interpretation, and application of stress echocardiography in schemic heart disease: from the American Society of Echocardiography." Journal of the American Society of Echocardiography 33.1 (Jan. 2020): 1-49.

Ratner, Alexander J., et al. "Data programming: Creating large training sets, quickly." Advances in neural information processing systems 29 (2016): 1-27.

Itu, Lucian Mihai, and Puneet Sharma. "Artificial intelligence for physiological quantification in medical imaging." U.S. Pat. No. 10,984,905. Apr. 20, 2021.

Senior, R., et al. "Stress echocardiography for the diagnosis and risk stratification of patients with suspected or known coronary artery disease: a critical appraisal. Supported by the British Society of Echocardiography." Heart 91.4 (2005): 427-436.

Sicari, Rosa, et al. "Exercise-electrocardiogramand/or pharmacological stress echocardiography for non-invasive risk stratification early after uncomplicated myocardial infarction. A prospective international large scale multicentre study." European heart journal 23.13 (2002): 1030-1037.

Stefani, Laura, et al. "Two-dimensional tracking and TDI are consistent methods for evaluating myocardial longitudinal peak strain in left and right ventricle basal segments in athletes." Cardiovascular ultrasound 5.1 (2007): 1-8.

* cited by examiner

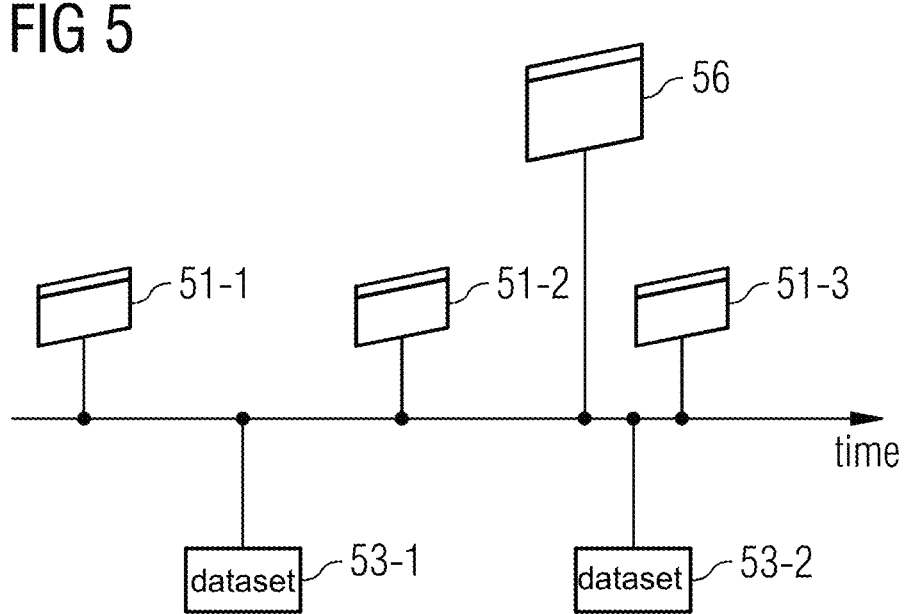
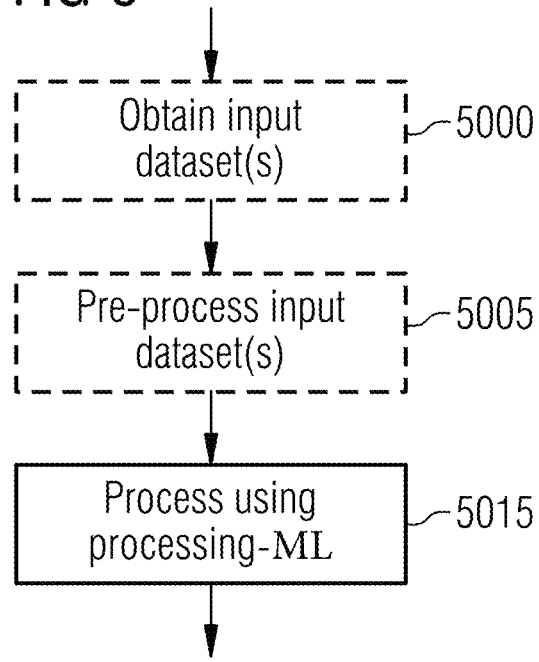

FIG 11B
Cloud-based clinical decision making solution for functional CAD assessment
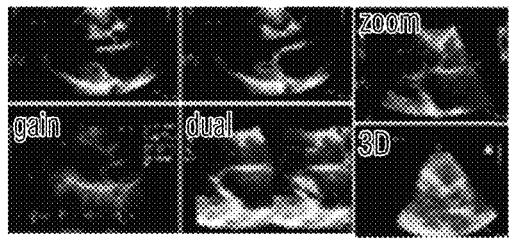
3004 — Echocardiographic view classification
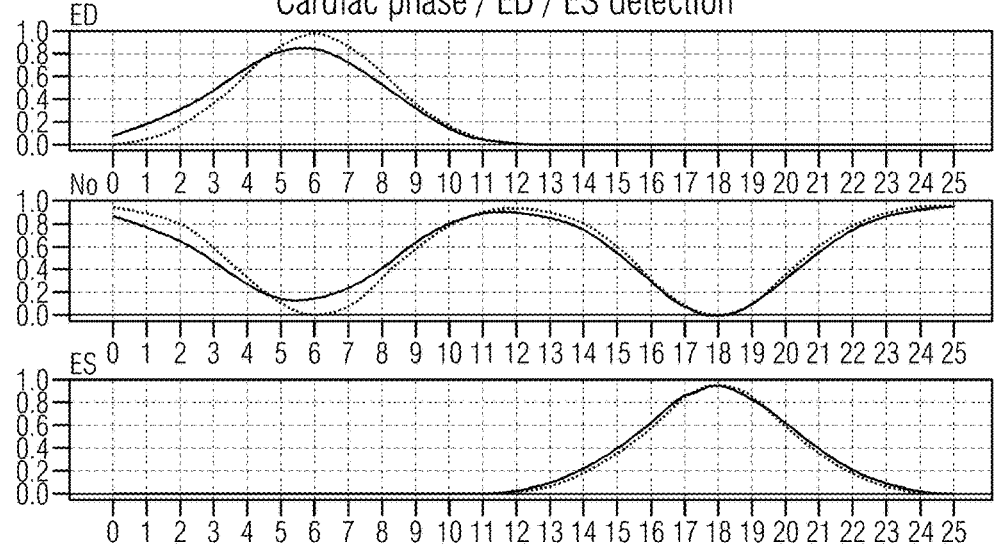
3005 — Cardiac phase / ED / ES detection
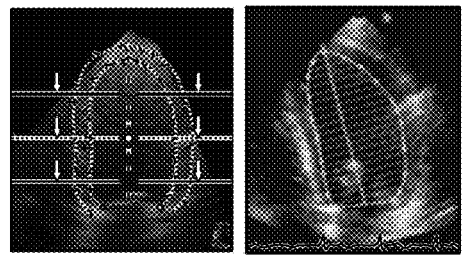
3006 — Segmentation & linear / volumetric measurements
110

CARDIAC FUNCTION ASSESSMENT USING MACHINE-LEARNING ALGORITHMS

RELATED APPLICATIONS

This application claims the benefit of EP 20465550.0, filed on Jul. 31, 2020 and DE 10 2020 209 696.1, filed Jul. 31, 2020, which are hereby incorporated by reference in their entirety.

BACKGROUND

Cardiovascular disease (CVD) is a leading cause of death worldwide. Among various CVDs, coronary artery disease (CAD) accounts for almost half of those death.

Various medical measurements including medical imaging and electrocardiograms are employed to characterize the fitness of the heart, blood vessels and blood (cardiovascular system).

It has been found that due to the multitude of available medical measurements, it is sometimes difficult to correctly assess the fitness of the heart. For example, it is sometimes difficult to comprehensively assess whether a patient has CAD or another CVD.

It is a critical aspect in the management of CVDs and treatment to accurately identify patients requiring medication and/or invasive measures and/or additional diagnostic tests and/or lifestyle changes. For example, in connection with the CAD, it is critical to accurately determine the fitness of the cardiovascular system in order to determine whether a patient should be scheduled for invasive coronary angiography and/or percutaneous coronary intervention.

The following documents of the prior art are known: Senior R, Monaghan M, Becher H, et al. Stress echocardiography for the diagnosis and risk stratification of patients with suspected or known coronary artery disease: a critical appraisal. Supported by the British Society of Echocardiography. Heart. 2005; 91:427-36; Heijenbrok-Kal M H, Fleischmann K E, Hunink M G. Stress echocardiography, stress single-photon-emission computed tomography and electron beam computed tomography for the assessment of coronary artery disease: a meta-analysis of diagnostic performance. Am Heart J. 2007; 154:415-23; Heimdal A, Stoylen A, Torp H, Skjaerpe T. Real-time strain rate imaging of the left ventricle by ultrasound. J Am Soc Echocardiogr 1998; 11:1013-1019; Leitman M, Lysyansky P, Sidenko S, Shir V, Peleg E, Binenbaum M et al. Twodimensional strain-a novel software for real-time quantitative echocardiographic assessment of myocardial function. J Am Soc Echocardiogr 2004; 17:1021-1029; Stefani L, Toncelli L, Gianassi M, Manetti P, Di Tante V, Vono M R et al. Twodimensional tracking and TDI are consistent methods for evaluating myocardial longitudinal peak strain in left and right ventricle basal segments in athletes. Cardiovasc Ultrasound 2007; 5:7; Alexander Ratner, Christopher De Sa, Sen Wu, Daniel Selsam, Christopher Ré, Data Programming: Creating Large Training Sets, Quickly, https://arxiv.org/abs/1605.07723; Cerqueira M D, Weissman N J, Dilsizian V, Jacobs A K, Kaul S, Laskey W K et al. Standardized myocardial segmentation and nomenclature for tomographic imaging of the heart. A statement for healthcare professionals from the Cardiac Imaging Committee of the Council on Clinical Cardiology of the American Heart Association. Circulation 2002; 105:539-542; Armstrong W F, Zoghbi W A. Stress echocardiography: current methodology and clinical applications. J Am Coll Cardiol 2005; 45:1739-47; Carlos M E, Smart S C, Wynsen J C, Sagar K B. Dobutamine stress echocardiography for risk stratification after myocardial infarction. Circulation 1997; 95:1402-10; Sicari R, Landi P, Picano E, Pirelli S, Chiaranda G, Previtali M, et al. Exercise-electrocardiography and/or pharmacological stress echocardiography for non-invasive risk stratification early after uncomplicated myocardial infarction. A prospective international large scale multicentre study. Eur Heart J 2002; 23:1030-7; Pellikka P A, Nagueh S F, Elhendy A A, Kuehl C A, Sawada S G. American Society of Echocardiography recommendations for performance, interpretation, and application of stress echocardiography. J Am Soc Echocardiogr 2007; 20:1021-41; Picano E. Stress echocardiography. 6th ed. Heidelberg: Springer Verlag; 2015; and L. Itu et al., artificial intelligence for physiological quantification in medical imaging, U.S. patent application Ser. No. 15/957,356.

SUMMARY

Accordingly, a need exists for advanced techniques to evaluate medical measurements of the cardiovascular system.

A method includes processing at least one input dataset using a multi-level processing algorithm. The multi-level processing algorithm includes a multi-task level and a consolidation-task level. An input of the consolidation-task level is coupled to an output of the multi-task level. The multi-task level is configured to determine multiple diagnostic metrics of the cardiovascular system based on the at least one input dataset. The consolidation-task level is configured to determine a fitness of the cardiovascular system of the patient.

The fitness could be associated with a CVD. The CVD could be CAD. Other types of CVDs that can be characterized by the fitness include: hypertensive heart disease; heart failure; valvular heart disease; cardiomyopathies; myocarditis; post cardiac surgery; cardiac arrhythmia and conduction disorders, e.g., left bundle branch block; ventricular pacing; right ventricle dysfunction caused by right ventricle pressure or volume overload.

The at least one input dataset can include imaging data or non-imaging data. For illustration, it would be possible that one or more of the at least one input dataset include imaging data of an echocardiography or stress echocardiography of the cardiovascular system of the patient. One or more of the at least one input dataset can include imaging data of a computed tomography of the cardiovascular system of the patient. One or more of the at least one input dataset can include a magnetic resonance tomography imaging data of the cardiovascular system of the patient. Another example is angiography.

The at least one input dataset could include context data associated with the patient, e.g., patient age, patient weight, pre-existing conditions, current and prior medications, lab values, etc.

The multi-task level can include one or more machine learning algorithms, e.g., artificial neural networks. The consolidation-task level can include one or more machine learning algorithms, e.g., artificial neural networks.

The multiple diagnostic metrics can include a classification of perspectives of use of imaging data of the at least one input dataset.

The multiple diagnostic metrics can include a classification of cardiac phases of the imaging data imaging the heart of the cardiovascular system.

The multiple diagnostic metrics can include a classification of anatomic features imaged by the imaging data of the at least one input dataset. This can be, in particular, helpful in scenarios in which multi-modality input data sets are obtained that can image different parts of the body of the patient.

The multiple diagnostic metrics can include a classification of properties of the left ventricle of the heart of the cardiovascular system.

The properties may be selected from: linear measurements; area measurements; cardiac deformation; volumetric measurements; mass; and/or segmentation.

The multiple diagnostic metrics may include a classification of a wall motion of the left ventricle of the heart of the cardiovascular system.

The multiple diagnostic metrics can include a classification of hemodynamics of a whole-body hemodynamic circulation associated with the cardiovascular system.

The consolidation-task level can be configured to determine the fitness of the cardiovascular system of the patient by classifying a wall motion of the left ventricle with respect to at least one or more of the following classes: normal response; ischemic response; necrotic response; viable response; normal; hypokinesis; akinesis; or dyskinesis.

It would be possible that the at least one input dataset includes multiple input datasets that are acquired at multiple stages of a disease of the cardiovascular system. Then, the consolidation-task level can be configured to determine a trend of the fitness across the multiple stages of the disease.

For instance, the stages could be selected from the group including: Suspected CAD; Stable CAD (chronic coronary syndrome); Post myocardial infarction; Acute CAD (e.g. unstable angina, acute myocardial infarction with STEMI and non-STEMI); post coronary revascularization; myocarditis, sarcoidosis, and cardiomyopathy.

Stages could be defined in accordance with major indications obtained from stress echocardiography, see, e.g., Sicari, Rosa, et al. "Stress echocardiography expert consensus statement: European Association of Echocardiography (EAE)(a registered branch of the ESC)." European Journal of Echocardiography 9.4 (2008): 415-437. This can include: CAD diagnosis; Prognosis and risk stratification in patients with established CAD (e.g. after myocardial infarction); Preoperative risk assessment; Evaluation of cardiac etiology of exertional dyspnea; Evaluation after revascularization; Ischemia location; Evaluation of heart valve stenosis severity.

For illustration, the trend of the fitness could indicate whether the health condition of the cardiovascular system increases or decreases. Changes in the diagnosis of presence of one or CVDs could be indicated. A perspective may be provided.

It would be possible that the at least one input dataset includes a medical report associated with the CVD. Then, the multi-level processing algorithm can be configured to extract at least one of the multiple diagnostic metrics from the medical report.

Such a technique can be, in particular, helpful in a scenario in which the trend of the fitness is determined across multiple stages of the CVD. In such a scenario, it is conceivable that not for all stages imaging data is available; rather, at least for some stages, a medical report drawn up by a medical practitioner and encoding one more diagnostic metrics in text form can be available. It would be possible that the at least one of the multiple diagnostic metrics is extracted by a preprocessing level of the multi-level algorithm.

Other tasks are conceivable to be implemented by the preprocessing level of the multi-level algorithm. For instance, it would be possible that the preprocessing level is configured to determine a quality index for one or more of the at least one input dataset and to optionally filter the at least one input dataset based on the quality index. For illustration, data of poor quality may be discarded. Alternatively or additionally to such filtering based on the quality index, it would also be conceivable that the multi-level preprocessing algorithm is configured to determine a confidence level of the fitness based on the quality index.

According to various examples, it would be possible to select between multiple configurations of a multi-level processing algorithm depending on at least one of the current stage of the CVD or the type of the CVD.

Such techniques can have the advantage that the respective algorithms determining, e.g., diagnostic metrics or the fitness, need not to be parameterized for all conceivable stages and/or types of the CVD; but can be rather tailored to specific types and/or stages of the CVD. Thereby, training of, e.g., a machine learning algorithm becomes simpler and less error prone.

At least one of the multi-task level and/or the consolidation-task level can include one or more neural networks that can be trained. This training can be based on the at least one input data set and one or more labeling functions. The one or more labeling functions can determine a ground truth for the at least one input data set. For illustration, it would be possible that the one or more labeling functions determine the ground truth based on a fractional flow reserve measurement, a clinical decision, a patient outcome, a stenosis grade determined based on a coronary angiography, or a wall motion score index otherwise determined. In particular, it would be possible that the one or more labeling functions consider a follow-up information obtained in other steps of the clinical workflow, subsequent to the determining of the fitness or the trend of the fitness of the cardiovascular system. This can correspond to unsupervised or reinforcement learning based on the information becoming available during inference. In other examples, supervised learning could be employed.

By using labeling functions, ground truth can be generated, e.g., based on follow-up information from the clinical workflow, without a need of heavy supervision. The labeling functions can adapt to missing input as is typical for clinical workflows which differ from patient to patient. The labeling function can provide accurate ground truth so as to increase the accuracy of the processing of the at least one input data set to determine the fitness of the cardiovascular system.

A method includes processing multiple input data sets indicative of at least one of measurements on a cardiovascular system of a patient or diagnostic metrics of the cardiovascular system. The processing uses at least one processing algorithm. The multiple input data sets are associated with different stages of a disease of the cardiovascular system. The at least one processing algorithm is configured to determine a trend of a fitness of the cardiovascular system across the multiple stages of the CVD.

For example, it would be possible that one or more of the multiple input data sets include a medical report associated with the disease of the cardiovascular system. The method can include preprocessing the one or more of the multiple input data sets including the medical report to extract associated one or more diagnostic metrics of the disease of the cardiovascular system.

The method could include determining a quality index for one or more of the multiple input data sets.

For example, it would be possible to filter one or more of the multiple input data sets. This can be based on the quality index. The filtering can be prior to processing the multiple input data sets using the at least one processing algorithm.

The at least one processing algorithm could be configured to determine a confidence level of the trend of the fitness based on the quality index.

It would be possible that the at least one processing algorithm is configured to provide a request for an additional measurement. The request can be based on the quality index. The request can be provided to a human-machine-interface and/or a control engine of a respective measurement apparatus capable to perform the respective measurement. The additional measurement can complement the multiple input data sets, e.g., fill-in missing information.

The at least one processing algorithm can be configured to select a subset of data from the multiple input data sets based on the trend of the fitness and to provide the subset of data to a human-machine-interface for expert review. Thereby, characteristic input datasets can be selected to illustrate the trend. This can facilitate expert review of a comparison between the input datasets underlying the trend.

The at least one processing algorithm could be implemented by a multi-level processing algorithm including a multi-task level and a consolidation-task level, as explained above. Each level can include one or more machine-learning algorithms, e.g., neural networks.

The at least one processing algorithm could be implemented by an auto-encoder neural network including an encoder and a decoder. The encoder is configured to determine an encoded representation of input data and the decoder is configured to determine, based on the encoded representation of the input data, output data that corresponds to a reconstruction of the input data.

For example, the trend of the fitness could be determined based on a comparison between the encoded representation of pairs of the input datasets obtained from the encoder of the auto-encoder neural network.

It would be possible that, for each one of the multiple input data sets, a subset of data is selected. The subsets of data of the multiple input data sets are compared with each other by the at least one processing algorithm. In particular, it would be possible to select the subsets of data to be compared based on matching content included in the subsets of data. For illustration, it would be possible that similar views of imaging data are selected for comparison. It would be possible that similar cardiac phases are selected for comparison. It would be possible that similar imaging data in terms of the underlying imaging modality is selected for comparison.

To determine whether content matches, it would be possible to employ one or more classification neural networks that provide respective classification of the data of the input data sets. In particular, it would be possible to employ a cascaded approach using, in a first stage, an auto-encoder neural network to determine the subsets, and in the second stage, an auto encoder neural network to determine the trend of the fitness, as explained above.

A method of training one or more neural networks of a multi-level processing algorithm is provided. The multi-level processing algorithm includes a multi-task level in the consolidation-task level. The multi-level processing algorithm is configured to determine a fitness of a cardiovascular system of a patient based on at least one input data set including medical measurements of the cardiovascular system. The method includes training the one or more neural networks based on the at least one input data set and one or more labeling functions. The one or more labeling functions determine a ground truth for the at least one input data set based on one more characteristics of a subsequent clinical procedure of treatment of the cardiovascular system.

The one or more labeling functions may be configured to receive one or more of the following inputs: a fractional flow reserve measurement; a clinical decision; a patient outcome; a stenosis grade determined based on a coronary angiography; a wall-motion score index.

Multiple neural networks of the multi-task level may be trained using multiple labeling functions. The multiple labeling functions have inter-dependencies.

A computer program or a computer-program product or a computer-readable storage medium includes program code. The program code can be loaded and executed by at least one processor. Upon executing the program code, the at least one processor is configured to perform a method. The method includes processing at least one input dataset using a multi-level processing algorithm. The multi-level processing algorithm includes a multi-task level and a consolidation-task level. An input of the consolidation-task level is coupled to an output of the multi-task level. The multi-task level is configured to determine multiple diagnostic metrics of the cardiovascular system based on the at least one input dataset. The consolidation-task level is configured to determine a fitness of the cardiovascular system of the patient.

A device includes at least one processor configured to process at least one input dataset using a multi-level processing algorithm. The multi-level processing algorithm includes a multi-task level and a consolidation-task level. An input of the consolidation-task level is coupled to an output of the multi-task level. The multi-task level is configured to determine multiple diagnostic metrics of the cardiovascular system based on the at least one input dataset. The consolidation-task level is configured to determine a fitness of the cardiovascular system of the patient.

A computer program or a computer-program product or a computer-readable storage medium includes program code. The program code can be loaded and executed by at least one processor. Upon executing the program code, the at least one processor is configured to perform a method. The method includes processing multiple input data sets indicative of at least one of measurements on a cardiovascular system of a patient or diagnostic metrics of the cardiovascular system. The processing uses at least one processing algorithm. The multiple input data sets are associated with different stages of a disease of the cardiovascular system. The at least one processing algorithm is configured to determine a trend of a fitness of the cardiovascular system across the multiple stages of the CVD.

A device includes at least one processor configured to process multiple input data sets indicative of at least one of measurements on a cardiovascular system of a patient or diagnostic metrics of the cardiovascular system. The processing uses at least one processing algorithm. The multiple input data sets are associated with different stages of a disease of the cardiovascular system. The at least one processing algorithm is configured to determine a trend of a fitness of the cardiovascular system across the multiple stages of the CVD.

For illustration, the device could be implemented by a medical measurement equipment. Alternatively or additionally, the device could be implemented by a server, e.g., of a hospital IT infrastructure.

It is to be understood that the features mentioned above and those yet to be explained below may be used not only in the respective combinations indicated, but also in other combinations or in isolation without departing from the scope of the invention.

BRIEF DESCRIPTION OF THE DRAWINGS

FIG. 5 schematically illustrates multiple datasets acquired at different points in time according to various examples.

FIG. 6 is a flowchart of a method according to various examples.

DETAILED DESCRIPTION OF EMBODIMENTS

Figure 1:
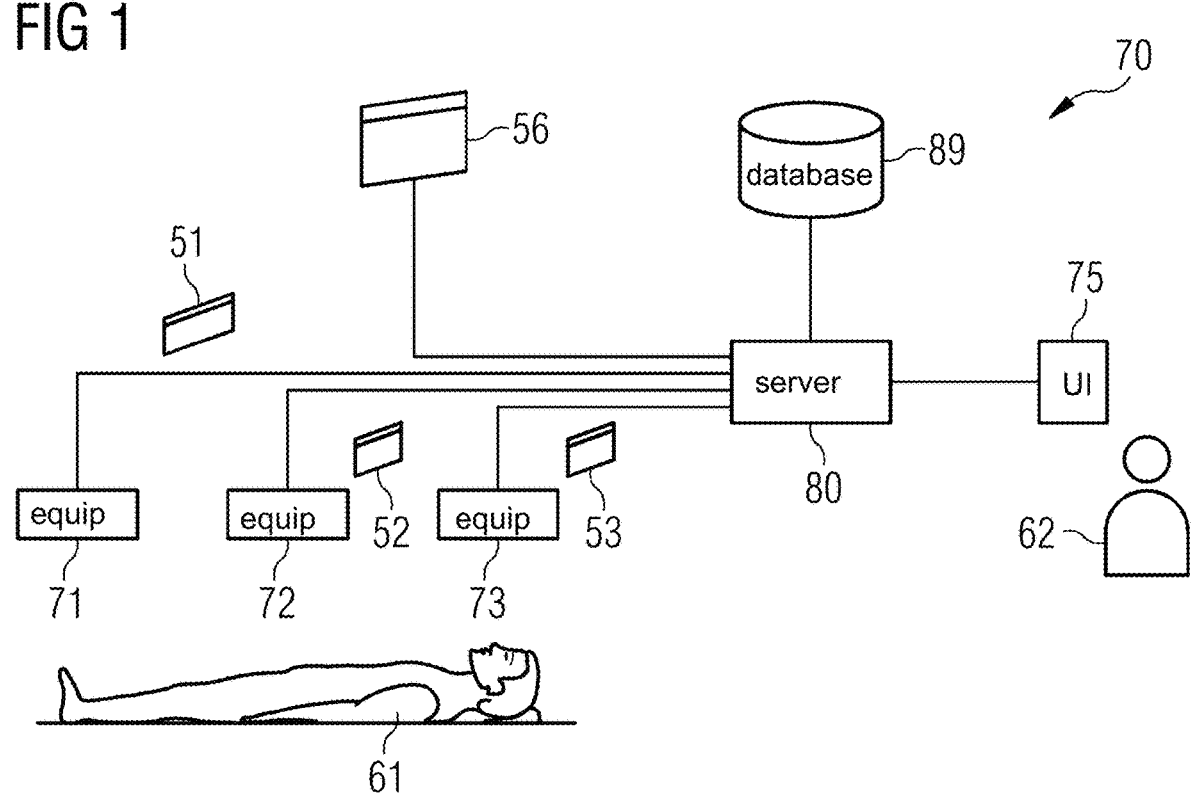
FIG. 1 schematically illustrates a system according to various examples, the system including multiple medical measurement apparatuses, a server, and a human-machine-interface.

Some examples of the present disclosure generally provide for a plurality of circuits or other electrical devices. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

In the following, embodiments will be described in detail with reference to the accompanying drawings. It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Hereinafter, techniques are described that facilitate estimating the fitness of a cardiovascular system of a patient. The fitness of the cardiovascular system can be indicative of a health level of the cardiovascular system. For example, the fitness of the cardiovascular system may be defined with respect to one or more CVDs, e.g., CAD. As a general rule, depending on the particular implementation, different metrics can be applied to estimate the fitness of the cardiovascular system. In some examples, it would be possible to estimate a risk factor or exposure to a particular CVD, e.g., the CAD. In other examples, it would be possible to generally assess the cardiac function of the cardiovascular system, e.g., assessing cardiac motion of the heart.

The techniques described herein can employ different information sources. For example, the techniques described herein can rely on one or more datasets that include information related to the patient. At least some of the one or more datasets can include information related to the cardiovascular system of the patient. It is also possible that at least one of the one or more datasets includes context information associated with the patient, e.g., medical reports, information regarding the patient, e.g., age, height, weight, medication, and/or pre-existing conditions, etc. At least one of the one or more datasets can be obtained using a medical measurement. For instance, at least one of the one or more datasets could include imaging data imaging the cardiovascular system of the patient. Different imaging modalities may be employed, e.g., stress echocardiography, magnetic resonance tomography (MRT), computed tomography (CT), ultrasound imaging, to name just a few. As a general rule, different ones of the one or more datasets can include imaging data of different imaging modalities. The one or more datasets are not limited to spatially-resolved imaging data, but could also include non-spatially-resolved measurement data such as electrocardiogram data, e.g., stress electrocardiogram data.

Alternatively or additionally to such a variation regarding the information content of the datasets, it is also possible that variations are used regarding the point in time at which respective information is acquired. According to some examples, multiple datasets may be available that are associated with different stages of a CVD. This means that different ones of the multiple input datasets are acquired at different points in time across the course of the CVD or, at least, across the course of changes to the fitness of the cardiovascular system.

According to the various examples described herein, it is possible to fuse such input datasets that have different information content and/or that are acquired at different stages of the CVD. In particular, such datasets can be used as input datasets to one or more algorithms that process the included information.

The techniques described herein enable processing input datasets using one or more algorithms and determine one or more indicators indicative of a fitness of the cardiovascular system based on such processing.

As a general rule, according to the various techniques described herein, it is possible to estimate the fitness of the cardiovascular system. For instance, it would be possible that one or more corresponding indicators are output by one or more algorithms. Such indicators can be indicative of one or more of the following: cardiac function, e.g., normal or abnormal or mildly-moderately-severely decreased; a trend of the fitness, e.g., a change in the cardiac function compared to prior studies, e.g., changed or unchanged; presence of a CVD, e.g., CAD detected or not detected; a risk of future cardiovascular events. As a general rule, the fitness could be determined for the current point in time or predicted for a future point in time.

Based on such one or more indicators, an expert, e.g., a medical practitioner, can then diagnose whether a certain CVD is present. The expert could mandate medication and/or further measurements including invasive measurements, and/or treatments including invasive treatments.

In the various techniques described herein, one or more processing algorithms can be used to process one or more input datasets. In particular, it is possible that at least one of the one or more processing algorithms employs machine learning.

A machine-learning (ML) algorithm can process data based on parameters that are set in a training phase. During training, values of these parameters are set based on a loss function. The loss function can describe a difference between an output of the ML algorithm—operating based on a training input dataset—and a ground truth associated with the training input dataset. By iteratively adjusting the values of these parameters in an optimization process, the loss function can be minimized or maximized. Weights of the ML algorithm are thereby determined. The ML algorithm can recognize one or more features based on the weights. These features are not empirically defined but are rather a consequence of the training process during the training phase. Examples of ML algorithms include artificial neural networks, support vector machines, genetic algorithms, kernel regression, discriminant analysis, or K-means, to name just a few further examples.

One particular imaging modality that can provide input datasets to the one or more algorithms to estimate the fitness of the cardiovascular system is echocardiography. Echocardiography is a non-invasive imaging examination using sound waves to provide a time-series of images of the heart and adjacent blood vessels. The assessment of the fitness of the cardiovascular system (cardiac function assessment) is often based on quantitative measurements, including ejection fraction (EF) and cardiac deformation (strain). Alternatively or additionally to such qualitative measurements, qualitative inferences can be made. For example, a qualitative interpretation of the underlying cardiac motion on a global and regional level would be possible. In clinical practice, the assessment of the cardiac function based on echocardiography is often repeated over time to determine a disease progression or therapy effect. Thus, echocardiography is typically performed at multiple stages of a CVD. A change in the cardiac function over time can have a significant impact on patient management decisions, e.g., whether to perform an interventional therapy or in patients with cancer whether to administer a full course of chemotherapy in case the cardiac function deteriorates as a side effect of the applied medication.

Accordingly, various techniques are based on the finding that it can be helpful to estimate a trend of the fitness of the cardiovascular system across multiple stages of a CVD. For example, it is possible to use one or more algorithms to determine the fitness, more specifically an indicator indicative of a trend of the fitness, e.g., across multiple stages of a CVD such as CAD.

One specific variant of echocardiography that can be used according to the described examples is stress echocardiography. Stress echocardiography has become a robust and cost-effective method for both the diagnosis and risk stratification of patients with suspected or known CAD. A characteristic of myocardial ischemia during stress echocardiography is the occurrence of reduced systolic wall thickening when myocardial oxygen demand exceeds myocardial blood supply. The induction of reduced regional systolic wall thickening is indicative of ischemia. Exercise, dobutamine, dipyridamole and adenosine echocardiography showed a sensitivity of 72-83% and a specificity of 84-91%, respectively, for a significant disease on invasive coronary angiography. This is similar to other non-invasive tests. Thus, there is a need to increase an accuracy in the determining of the fitness of the cardiovascular system, e.g., in the context of a diagnosis of CAD. It is possible to increase this accuracy using techniques described herein.

Various techniques are based on the finding that traditional approaches to the assessment of severe CAD are based on the extraction of measurements from various imaging modalities. The intrinsic limitation of such prior-art approaches is that they rely on quality and reproducibility of the measurements which cannot be guaranteed in real life clinical practice. This results in clinical guidelines recommending a limited amount of input data to enable accuracy and reproducibility in the assessment. In many cases such measurements are only designed to support qualitative assessments, e.g., 'normal' versus 'abnormal' wall motion of the left ventricle, because of intrinsic issues such as inter-user, intra-user, and inter-vendor variability.

Various techniques described herein facilitate jointly considering multiple sources of information within an automated processing pipeline. A priori constrains can be lifted or mitigated. ML algorithms can be employed to provide an indicator indicative of the fitness of the cardiovascular system of a patient. By employing one or more ML algorithms, the one or more ML algorithms can freely explore, during the training phase, the relevance of multiple features such as image feature, non-image features and combinations thereof, thereby identifying the patterns that yield the most accurate classification.

Various techniques are based on using at least one ML algorithm to support clinical decision for CVDs. For example, it would be possible to accurately identify, from stress echocardiography, the suspected/known CAD patients which require coronary revascularisation, i.e., should be scheduled for invasive coronary angiography. Such techniques can be helpful to support clinical decision across different stages of the pathology of the CAD.

The techniques described herein can comprehensively analyze input datasets associated with current and prior measurements or studies of the cardiovascular system. An automated ML algorithm can comprehensively analyze the input datasets from current and prior studies both quantitatively and qualitatively.

For instance, such techniques can integrate, firstly, methods for anatomical and functional assessment of the fitness of the cardiovascular system, e.g., based on stress echocardiography or other measurements; and, secondly, methods for hemodynamic assessment of the cardiovascular system, specifically, the heart.

It would be possible to process at least one input dataset using at least one processing algorithm. The at least one processing algorithm can include a ML algorithm, e.g., an artificial neural network including an input layer, an output layer, and multiple hidden layers. Each hidden layer may perform one or more of the following operations: convolution, (non-linear) activation, pooling, etc. Alternatively or additionally, the at least one processing algorithm could also include an empirically parametrized model of the cardiovascular system. Based on the processing using the at least one processing algorithm, it is possible to determine a fitness of the cardiovascular system of the patient. For instance, the fitness could indicate whether the cardiac function is impaired. For instance, the fitness could indicate whether one or more risk factors for presence of a CVD are detected.

For example, it would be possible to process, using the at least one processing algorithm, multiple input datasets. The multiple input datasets can be indicative of at least one of measurements on a cardiovascular system of a patient or diagnostic metrics of the cardiovascular system. The multiple input datasets are acquired at different stages of a pathology of the cardiovascular system. The at least one processing algorithm is then configured to determine a trend of the fitness of the cardiovascular system across the multiple stages of the pathology.

By determining the trend of the fitness of the cardiovascular system across the multiple stages of the pathology, it is possible to accurately assess—e.g., qualitatively and/or qualitatively—whether the fitness—e.g., associated with a CVD—worsens or improves. Thereby, it is possible to assist an expert in the diagnosis and potentially the treatment planning. Such techniques can also help with prognosis/risk stratification.

As a general rule, there are various options available for implementing the at least one processing algorithm. According to some examples, the at least one processing algorithm can be implemented as a multi-level processing algorithm. Such multi-level processing algorithms can implement a stacked hierarchy in which data is sequentially processed using multiple sub-algorithms associated with the different levels. Here, each level may include one or more sub-algorithms. Sub-algorithms of a given level can be arranged in parallel and/or sequentially. Such a multi-level processing algorithm helps to more accurately determine the fitness of the cardiovascular system, because the sub-algorithms of the multiple levels can be specifically configured to perform certain inference tasks. Where ML algorithms are employed, more accurate training can be performed, because the training process can be broken down into subtasks which are easily handled by the individual sub-algorithms. For empirically parametrized models implementing the sub-algorithms, it is possible to limit the amount of processed information, thereby making it possible to determine certain specific aspects of characteristics of the cardiovascular system.

For illustration, the multi-level processing algorithm can include a multi-task level and a consolidation-task level. Here, an input of the consolidation-task level is coupled to an output of the multi-task level. I.e., in the processing pipeline, the consolidation-task level is arranged downstream of the multi-task level. The multi-task level is configured to determine multiple diagnostic metrics of the cardiovascular system based on the at least one input dataset. Then, the consolidation-task neural network level is configured to determine a fitness of the cardiovascular system of the patient.

FIG. 1 schematically illustrates aspects with respect to a system 70 that can be employed to assist a medical practitioner 62 in the diagnosis and treatment of CVDs of a cardiovascular system of a patient 61. The system 70, accordingly, supports cardiac function assessment.

The system 70 includes measurement equipment 71, 72, 73. The measurement equipment 71-73 is configured to acquire measurement data, e.g., imaging data and/or time-series data, etc. The measurement equipment 71-73 is configured to provide datasets 51-53 to a server 80 based on the measurement data. For example, a given dataset 51-53 can aggregate multiple measurement data, include a respective header and/or type information, etc.

The server 80—e.g., part of an enterprise healthcare IT environment—also is configured to receive further datasets 56 that are not acquired using measurements on the patient 61. For instance, these further datasets 56 could include context data associated with one or more patient characteristics of the patient 61, e.g., patient age, patient weight, patient pre-existing conditions, etc. Alternatively or additionally, such further datasets 56 could include medical reports in text form of previous measurements on the patient.

The server 80 is also coupled with the database 89. The database 89 could be an external database were physically integrated with the server 80. For instance, one or more of the datasets 51-53, 56 can be stored in the database 89 before processing the one or more datasets 51-53, 56. Thereby, it would be possible to pertain datasets associated with multiple stages of a CVD.

While FIG. 1 illustrates a single database 89, as a general rule, distributed storage systems and/or multiple databases may be used. Multiple databases may be physically located at different storage entities, e.g., remotely from each other. It would be possible that distributed storage systems and/or multiple databases store redundant copies of the data or different parts of the respective data.

The server 80 is configured to process one or more datasets—e.g., the datasets 51-53, 56—in order to estimate a fitness of the cardiovascular system of the patient 61. One or more indicators indicative of the fitness can be output to a human machine interface 75, thereby making it available to the practitioner 62.

While in the scenario of FIG. 1 there is provisioned the server 80 to estimate the fitness of the cardiovascular system, it is possible that such functionality is implemented on a processing circuitry of one or more of the measurement equipment 71-73. Thus, it may not be required in all scenarios to provision a separate server 80.

Alternatively or additionally, it would also be possible to provide control data to one or more of the measurement equipment 71-73 based on the one or more indicators indicative of the fitness, to thereby control further measurements of the patient 61. For instance, further measurements can be triggered, e.g., in case the indicator indicative of the fitness indicates a deteriorated fitness of the cardiovascular system, e.g., an acute CAD. Alternatively or additionally to such control data that triggers further measurements, it would be possible that control data is provided that triggers further processing of measurement data. For instance, further quantifications could be executed, e.g., to obtain additional indicators from the measurement data.

Figure 2:
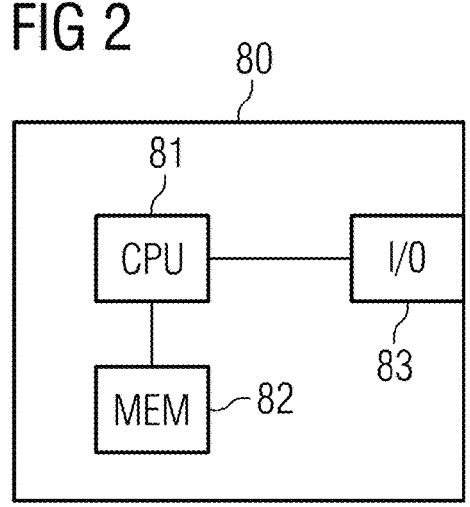
FIG. 2 schematically illustrates details of the server according to various examples.

FIG. 2 schematically illustrates aspects with respect to the server 80. The server 80 includes control circuitry, here implemented by a processor 81 and a non-volatile memory 82. The processor 81 can load program code from the non-volatile memory 82 and execute the program code. The processor 81 can communicate via an interface 83 with, e.g., measurement equipment 71-73 and/or a human machine interface 75 and/or the database 89. The processor 81, upon loading and executing the program code, the processor can perform one or more of the following techniques as described herein in further detail: processing one or more input datasets using one or more algorithms, e.g., including at least one ML algorithm; controlling operation of the measurement equipment 71-73; storing data, e.g., an output of the one or more algorithms in the database 89; providing data, e.g., an output of the one or more algorithms to the human-machine-interface 75; etc.

Figure 3:
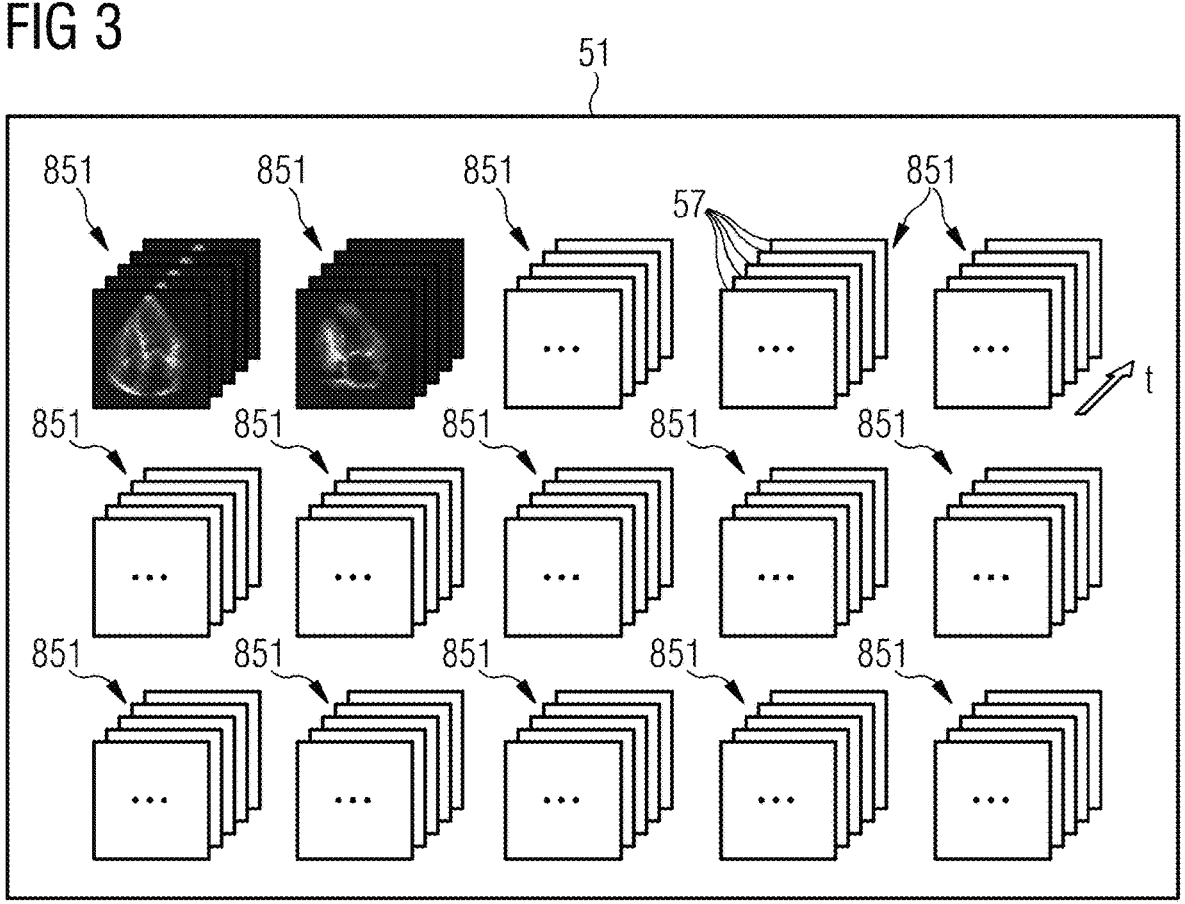
FIG. 3 schematically illustrates a time-series of imaging data of a dataset acquired using a medical imaging measurement according to various examples.

FIG. 3 schematically illustrates aspects with respect to an example implementation of the dataset 51. In the illustrated example, the dataset 51 includes imaging data in the form of multiple time series 851 each including multiple frames 57 (movie). For instance, an echocardiography movie could be provided by the multiple frames 57. Here, wall motion of the heart can be captured. Another option would be CT or MRT using a contrast agent. MRT can make blood flow visible.

As a general rule, each dataset 51 may include one or multiple movies. For instance, different movies of a dataset 51 may be associated with different perspectives. For example, different movies of a dataset 51 may be associated with different measurement parameters, e.g., with contrast agent or without contrast agent, patient under stress or no stress, etc.

Figure 4:
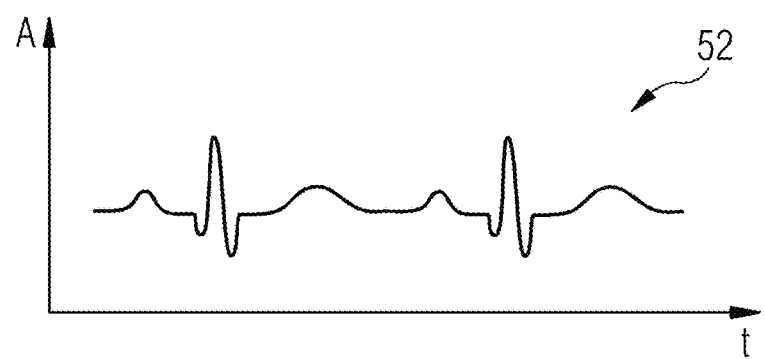
FIG. 4 schematically illustrates a time-series of data acquired using a medical measurement according to various examples.

FIG. 4 schematically illustrates aspects with respect to an example implementation of the dataset 52. In the illustrated example, the dataset 52 specifies an electrocardiogram that is time resolved. Illustrated are two heartbeats.

The time resolution pertains to a measurement at a given stage of a CVD. Sometimes, it is possible to obtain multiple datasets at different stages of a CVD. This is illustrated in connection with FIG. 5.

FIG. 5 schematically illustrates multiple datasets 51-1, 51-2, and 51-3—e.g., each dataset including one or more echocardiography movies, as discussed in connection with FIG. 3—being acquired at different stages of a CVD. For instance, the time between acquisition of the multiple datasets 51-1, 51-2, and 51-3 could be hours or days or weeks or years. It is also illustrated that over the course of time different datasets 51-1-51-3, 53-1-51-2, 59 can be acquired or established, e.g., in an interleaved fashion and at different points in time. Despite such time domain offsets and distributions as illustrated in FIG. 5, it is possible to process these datasets 51-1-51-3, 53-1-53-2, and 59.

According to various techniques described herein, it is possible to process datasets 51-1-51-3, 52, 53-1-53-2, 56 of different types (e.g., different measurement types, different imaging modalities, pertaining to context data, etc.) and/or associated with different stages of a CVD. One example technique for such processing is illustrated below in connection with FIG. 6.

FIG. 6 is a flowchart of a method according to various examples. For illustration, the method of FIG. 6 could be executed by the server 80, e.g., by the processor 81 upon loading program code from the memory 82. Optional boxes are marked with dashed lines in FIG. 6.

FIG. 6 illustrates aspects with respect to processing one or more input datasets. For instance, at box 5000, one or more of the input datasets 51-53 can be obtained from different measurement equipment 71-73, as discussed in connection with FIG. 1. Alternatively or additionally, it would be possible to obtain an input dataset 56 including context data, e.g., medical reports and/or a patient information. Such an input dataset including context data may be obtained from a hospital information system or a patient-related database. Alternatively or additionally, it would also be possible to obtain multiple input datasets associated with different stages of a CVD. For example, it would be possible to process the multiple datasets 51-1-51-3 (cf. FIG. 5).

At box 5000, one or more measurement equipment may be controlled to acquire and/or provide one or more input datasets. For instance, this can involve acquiring imaging data, e.g., using a stress echocardiography, CT and/or MRT, to name just a few example imaging modalities. Further, multi-modality imaging would be possible, using multiple imaging modalities, thereby acquiring multiple datasets associated with the multiple imaging modalities.

Alternatively or additionally to controlling one or more measurement equipment, it would be possible to load at least one of the one or more input datasets from a database (e.g., database 89) or another memory.

Figure 7:
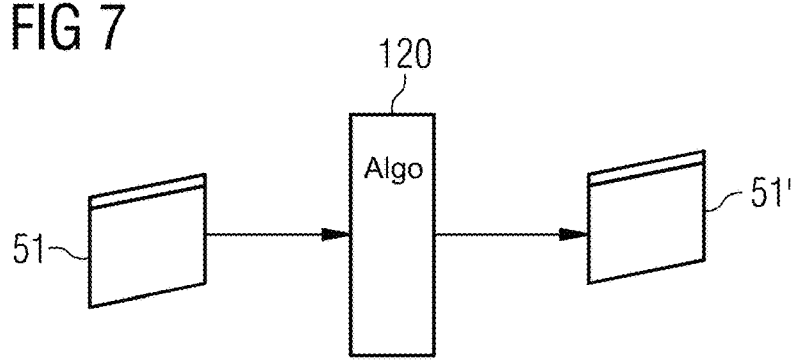
FIG. 7 schematically illustrates a preprocessing algorithm configured to process an input dataset according to various examples.
Figure 8:
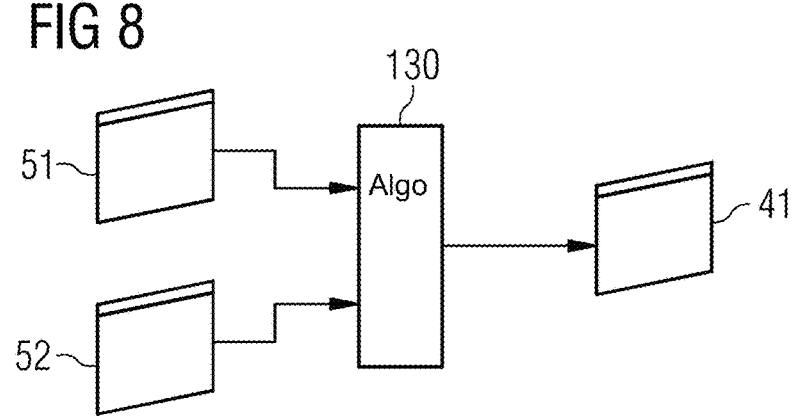
FIG. 8 schematically illustrates a preprocessing algorithm configured to process multiple input datasets according to various examples.

At box 5005, the one or more input datasets—obtained at box 5000—can be preprocessed. Here, it is possible that at least one of multiple input datasets is preprocessed. For the preprocessing at box 5005, a preprocessing algorithm—e.g., implemented as an empirically parametrized algorithm or a ML algorithm—may be employed. This is illustrated in connection with FIG. 7. Here, a preprocessing algorithm 120 receives, as the input, the input dataset 51 and outputs to preprocessed input dataset 51'. Another example implementation of preprocessing is illustrated in connection with FIG. 8. Here, a preprocessing algorithm 130 receives multiple input datasets 51, 52 and outputs a new (inferred) dataset 41. The dataset 41 can be indicative of one or more hidden observables associated with the CVD. Hidden observables may not be directly accessible based on measurement. Rather, such hidden observables may be derived from measured quantities, here represented by the input datasets 51, 52 (in other examples, it would be possible that hidden observables are derived using the preprocessing algorithm 130 from only a single input dataset or more than two input datasets). One example of such preprocessing to derive one or more hidden observables would be a hemodynamic analysis where a lumped parameter model of the cardiovascular system may be employed to generate personalized hemodynamic measures-of-interest of the circulation and, in particular, the left ventricle (LV) of the cardiovascular system. For the parameterization of the model, one or more characteristics may be extracted from the medical images of the input datasets input to the preprocessing algorithm 130, e.g., ejection time, regurgitation, time-varying volume. Based on such observables, it is possible to parametrize the model. Alternatively or additionally to such an empirically parametrized whole-body circulation hemodynamic model, it would be possible to employ an ML algorithm to derive characteristics of the blood circulation. This is based on the finding that although each forward-run with an empirically-parametrized hemodynamic model is efficient in terms of computation time, the multitude of runs required for the personalization can lead to a runtime of up to one minute on the standard hardware configuration. Hence, a machine-learning surrogate algorithm of the empirically parametrized hemodynamic model may be employed, capable of predicting output measures in real time with values that are statistically distinguishable from those obtained with the conventional empirically-parametrized hemodynamic model. An example is described in U.S. patent application Ser. No. 15/957,356.

Referring again to FIG. 6: Preprocessing at box 5005 can take different forms according to different example implementations. For illustration, it would be possible to discard low-quality data of the one or more input datasets. For example, the quality of the data of the one or more input datasets can be estimated, e.g., using a quality metric. For this, one or more characteristics of the data of the one or more input datasets can be checked against the quality metric. For instance, it would be possible to detect a noise floor; the noise floor could be compared against a threshold. Alternatively or additionally, it would be possible to detect imaging artefacts, e.g., blindspots, motion blur, convolutions for MRT, etc. and then rate the quality using the quality metric. Where one or predefined criteria in accordance with the quality metric cannot be met, respective data may be discarded.

Such filtering of low quality data as explained above is only one example of preprocessing that could take place at box 5005. Other forms of preprocessing conceivable. For example, where multiple input datasets acquired with different imaging modalities are obtained, it would be possible to synchronize data between the multiple imaging modalities. This can involve shifting a time base back and forth so as to align the timing of, e.g., the time series of data of a first imaging dataset with the timing of a time series of data of a second imaging dataset. For instance, it would be conceivable that an echocardiography movie is time-aligned with a time series of an electrocardiogram.

Next, at box 5015, the one or more input datasets are processed in one or more processing algorithms. At least one processing algorithm of the one or more processing algorithms can include a ML algorithm. Hereinafter, various examples will be described in the context of an implementation of a ML algorithm as an artificial neural network (NN), but similar techniques may be readily applied to other types of ML algorithms.

Next, details with respect to an implementation of the one or more processing algorithms of box 5015 will be explained. One example implementation as illustrated in connection with FIG. 9.

Figure 9:
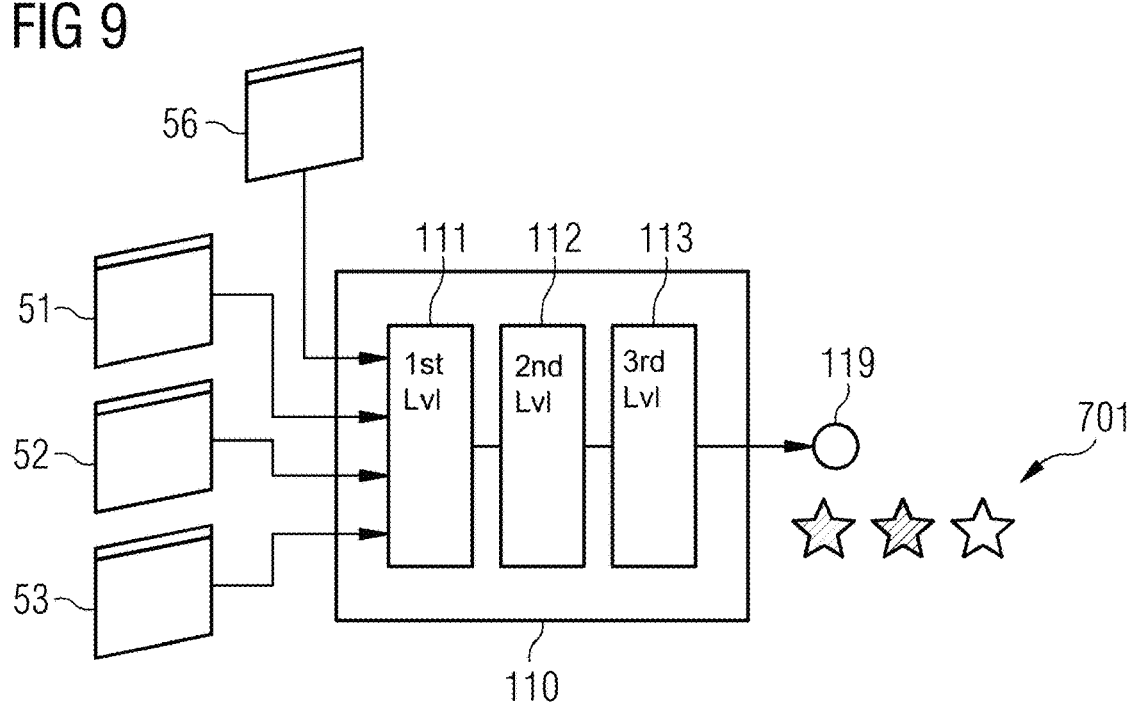
FIG. 9 schematically illustrates a multi-level processing algorithms according to various examples.

FIG. 9 schematically illustrates aspects with respect to processing of multiple input datasets, here the input datasets 51-53, 56. In the scenario of FIG. 9, the multiple input datasets 51-53, 56 are processed using a multi-level processing algorithm 110. The multi-level processing algorithm 110 includes, in the illustrated example, three levels 111, 112, 113 arranged in sequence. The multi-level processing algorithm is configured to determine an output 119 that is indicative of the fitness of the cardiovascular system of the patient.

For example, in the illustrated scenario, the output 119 includes a fitness score 701 associated with the fitness of the cardiovascular system of the patient. Other implementations of indicating the fitness of the cardiovascular system would be possible, e.g., an indicator indicative of whether CAD is likely or not.

In the multi-level processing algorithm 110, the different levels 111-113 can have different tasks. Some of the levels 111-113 can have multiple tasks while others may have single tasks.

Figure 10:
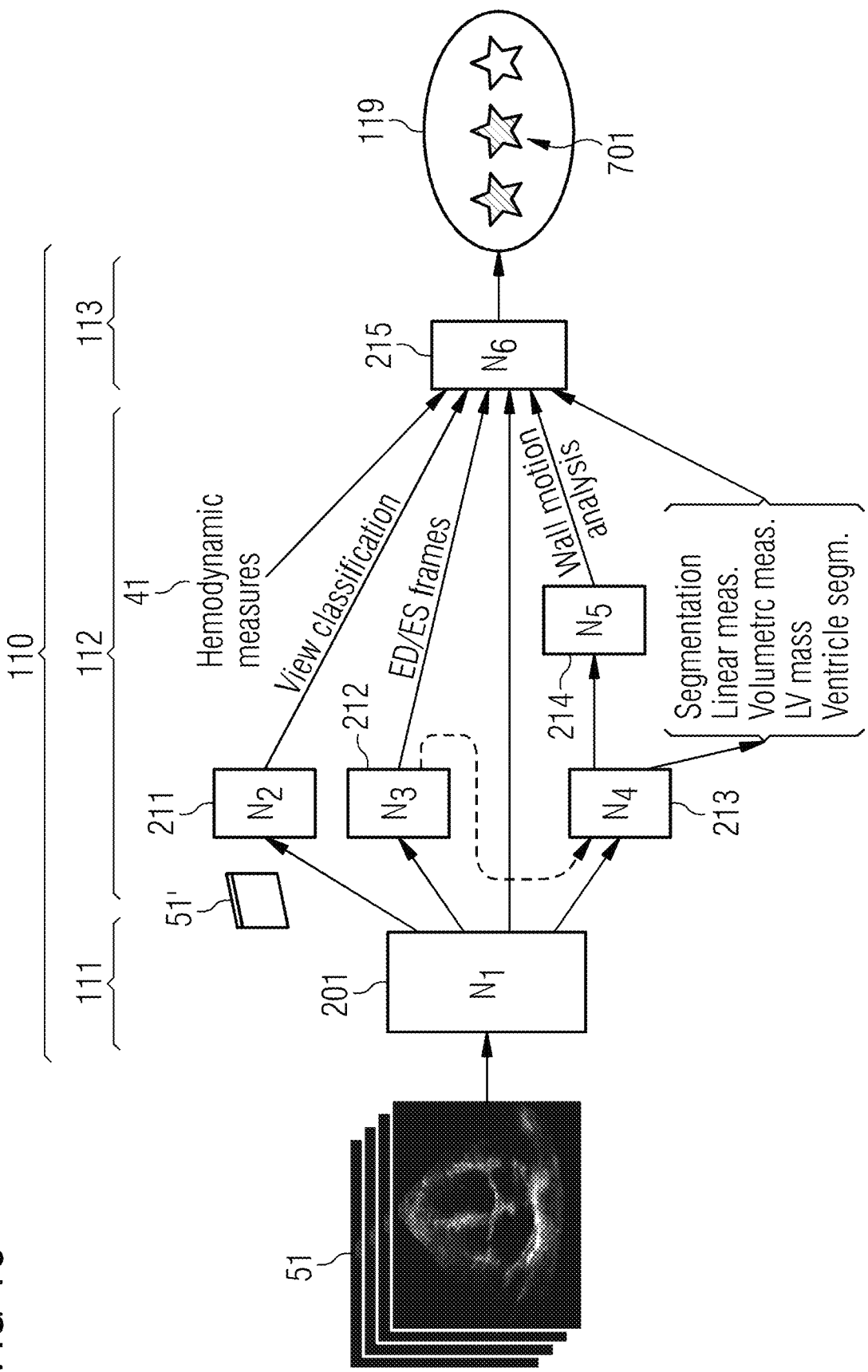
FIG. 10 schematically illustrates details of the multi-level processing algorithm of FIG. 9 according to various examples.

One specific example implementation of the multi-level processing algorithm 110 is illustrated in FIG. 10. In the example of FIG. 10, the multi-level processing algorithm 110 includes three levels 111, 112, and 113.

As a general rule, it would be possible that the multiple levels of the multi-level processing algorithm 110 are trained separately or in an end-to-end fashion.

The level 111 implements preprocessing. As such, the preprocessing of the level 111 complements or replaces a separate preprocessing algorithm 120, 130 (cf. FIG. 7 and FIG. 8).

In the example of FIG. 10, frames of a time series of electrocardiography imaging data of the input dataset 51 are preprocessed using the algorithm 201 of the preprocessing level 111. The algorithm 201 is implemented as a NN. For example, artifacts or noise may be reduced or suppressed.

The pre-processing level 111 is generally optional.

Next, a multi-task level 112 is provided including multiple NNs 211-214, wherein the NNs 211, 212, and 213/214 are arranged in parallel and the NNs 213 and 214 are sequentially arranged in the multi-task level 112.

The multi-task level 112 is configured to determine multiple diagnostic metrics of the cardiovascular system, here based on the preprocessed input dataset 51'.

The multiple diagnostic metrics include a classification of perspectives of views in the imaging data of the input dataset 51. For this, the NN 211 is provided and classifies the perspectives of the multiple one or more views, e.g., specifically of frames of the time-series of the imaging data of the input dataset 51. This is based on the finding that a prerequisite for analyzing, e.g., the wall motion on echocardiography images is the accurate identification of the perspectives. The perspectives of interest are typically the parasternal long axis view, the parasternal short axis view, the apical four chamber view, and the apical 2 chamber view. Respective labels may be assigned to each frame.

As a general rule, such classification of the perspective or perspectives of imaging data included in one or input datasets may be applicable to other kinds and types of imaging data, beyond echocardiography.

The multiple diagnostic metrics also include a classification of cardiac phases depicted by frames over time-series of frames of the imaging data included in the input dataset 51. For example, the systole and the diastole can be discriminated from each other. Respective labels may be assigned to each frame (e.g., "ED[iastole]" and "ES[ystole]" in FIG. 10). This is achieved using the NN 212.

A further one of the multiple diagnostic metrics includes classification of anatomic features imaged by the imaging data included in the input dataset 51. For instance, it would be possible to detect the particular anatomy imaged by the imaging data. For example, this can be in particular relevance in case the particular measurement modality can be flexibly used to image different parts of the anatomy of a user, e.g., as would be the case for CT or MRT.

Yet a further example of the multiple diagnostic metrics includes a classification of properties of the LV of the heart. The properties could be selected from the group: linear measurement; volumetric measurements; LV mass; ventricle segmentation. This is implemented by the NN 213. As a general rule, various examples of features that can be classified are conceivable. For instance, linear measurements could be performed, e.g., distances, thicknesses, etc. Here, linear measurements of the LV and its walls may be performed in the parasternal long-axis view. Volumetric measurements would be conceivable. For example, a time-varying volume, end-systolic volume, end-diastolic volume, or the ejection fraction may be measured. (Note that for this the NN 213 can receive the output of the NN 212, as indicated by the dashed line). The LV segments in the 16-, 17-, or 18-segment model may be measured. For example, details with respect to such classification are described in American Heart Association Writing Group on Myocardial Segmentation and Registration for Cardiac Imaging: et al. "Standardized myocardial segmentation and nomenclature for tomographic imaging of the heart: a statement for healthcare professionals from the Cardiac Imaging Committee of the Council on Clinical Cardiology of the American Heart Association." *Circulation* 105.4 (2002): 539-542.

The LV mass can be computed for measurements at end-diastole. Interventricular septum, LV internal diameter; end inferolateral wall thickness are further examples of properties of the LV that can be determined by the NN 213.

The diagnostic metrics can further include a classification of wall motion of the LV. This is sometimes referred to as regional wall motion analysis. For the rest state and for the states corresponding to different dobutamine/exercise levels, a wall motion score index (WMI) can be assigned to each segment based on its systolic function.

For example, normal=1; hypokinesis=2; akinesis=3; dyskinesis=4. The index (wall motion systolic index) can be determined by a NN 214 that is coupled to the output of the NN 213 that is configured to classify the properties of the LV, e.g., using linear segmentation (thereby, labeling the position of the LV walls). For example, the WMI could be calculated by dividing the sum of the wall motion scores of each segment by the total number of segments. For training of the NN 214, ground truth information may be defined based on expert annotations performed by visual analysis. Different variations between different states are expected to be encountered for stable and acute CAD patients. The WMIs could be visualized in a polar plot.

In another example, it would be possible that the WMI is indicative of a classification of a wall motion of the LV of the heart with respect to one or more of the following classes: normal response, ischemic response; necrotic response; viable response. Such techniques are based on the finding that another important application of stress echocardiography is its use in the postmyocardial infraction setting. After myocardial infarction, stress echocardiography allows for the assessment of resting global and regional ventricular function, identification of the presence and extends of peri-infarction and remote ischemia, resting left ventricular dysfunction, the extent of wall motion abnormality (WMA) at rest, extending threshold of inducible ischemia, and the absence of myocardial viability during stress identify high-risk patients not predictive of worse prognosis. Further, failure to revascularize patients with viable myocardium identified by stress echocardiography may lead to worse outcomes. Stress echocardiographic diagnosis can be summarized into categories centered on the regional wall function describing the fundamental response patterns. Thus, the multi-level algorithm 110 can be used to output a categorical variable of the fitness that is based on the WMI indicative of ischemic response, the necrotic response, and the viable response. The normal response classifies a segment of the wall as normokinetic at rest and normal or hyperkinetic during stress. The ischemic response is indicative that the function of a segment worsens during stress from normokinetic to hypokinesia (decrease of endocardial movement and systolic thickening), akinesia (absence of endocardial movement and systolic thickening), or dyskinesia (paradoxical outward movement and possible systolic thickening). However, a resting akinesia becoming dyskinesia during stress reflects purely passive phenomenon of increased intra-ventricular pressure developed by normally contracting walls and should not be considered a true active ischemia. The necrotic response is indicative of a segment with resting dysfunction that remains fixed during stress, i.e., does not improve. The viable response is indicative of a segment with resting dysfunction that may show either a sustained improvement during stress indicating a non-jeopardized myocardium (stunned) or improve during early stress with subsequent deterioration at peak (biphasic response). The biphasic response is suggestive of viability and ischemia, with jeopardized myocardium fed by a criticality diseased coronary stenosis.

Above, various examples have been described in the context of a wall motion analysis in the context of a CAD. However, as mentioned above, the techniques described herein are not limited to the presence of CAD, but rather other CVDs would be conceivable as well. For example, abnormal motion patterns of the interventricular septum may be found post cardiac surgery or in the presence of a left bundle branch block or ventricular pacing, as well as right ventricle dysfunction caused by right ventricle pressure or volume overload.

As explained above, different categories of the WMI can be defined depending on the type and/or the stage of the CVD. It would be possible that different configurations of the respective algorithm to determine the WMI are selected depending on the type and/or the stage of the CVD. This can also apply to further parts of the multi-level algorithm 110. As a general rule, it would be possible to select between multiple configurations of the multi-level processing algorithm depending on the stage and/or type of the CVD.

As a general rule, the WMI can be provided per segment, i.e., spatially resolved, or as an overall score for the heart.

The consolidation level 215 includes an NN 215. The NN 215 receives, as an input, the output of the multi-task level 112, i.e., of the NNs 211-214. Based on this, the NN 215 determines the output 119, indicative of the fitness 701 of the cardiovascular system. Based on such indicator, it would be possible to take a clinical decision of invasive coronary angiography and/or percutaneous coronary intervention.

As illustrated in FIG. 10, a further input of the NN 215 of the consolidation task level 113 can be the hemodynamics measure 41, e.g., as obtained from the preprocessing algorithm 130. Alternatively or additionally to using a separate preprocessing algorithm 130—that would normally not be trained along with the NNs 211-215 of the multi-level algorithm 130 (but rather be separately trained or parametrized), it would also be possible that the multitask network level 112 or the preprocessing network level 111 includes a respective algorithm to determine the hemodynamics measure 41, i.e., the diagnostic metrics of the multitask network level 112 further include the hemodynamic measure.

In case the fitness 701 of the output 119 indicates that the coronary circulation requires revascularization, also the corresponding coronary artery may be indicated, e.g., LAD, LCx, RCA. This may be done as a postprocessing step, based on the LV segments displaying an abnormal wall motion.

A possible clinical workflow of data processing associated with the multi-level processing algorithm 110 as illustrated in connection with FIG. 11.

Figure 11:
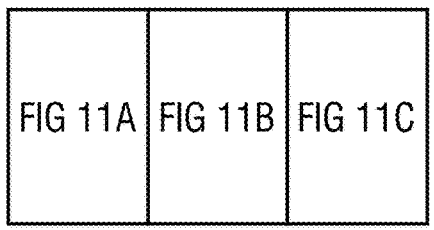
FIG. 11 represents a combination of FIGS. 11A-C, which combination schematically illustrates a clinical decision support workflow for supporting the assessment of a CVD or, more generally, the fitness of the cardiovascular system of a patient according to various examples.
Figure 11A:
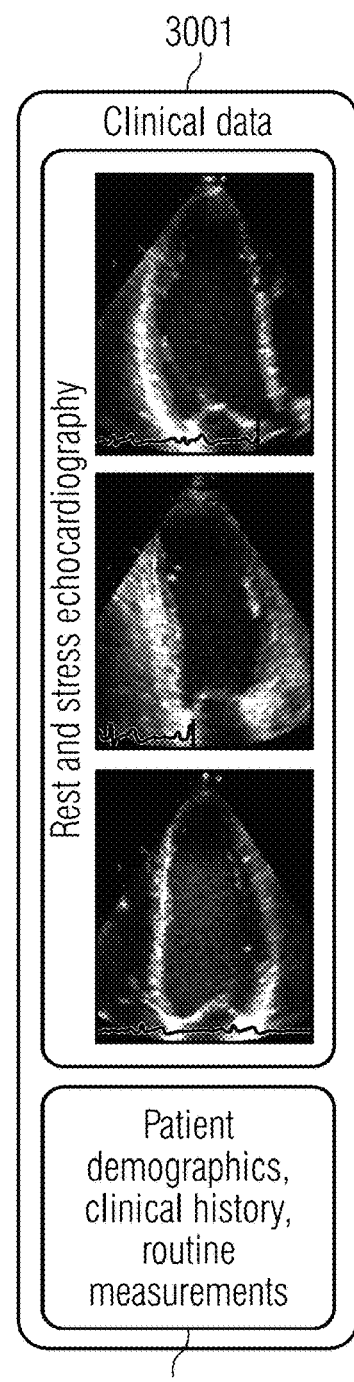
Figure 11C:
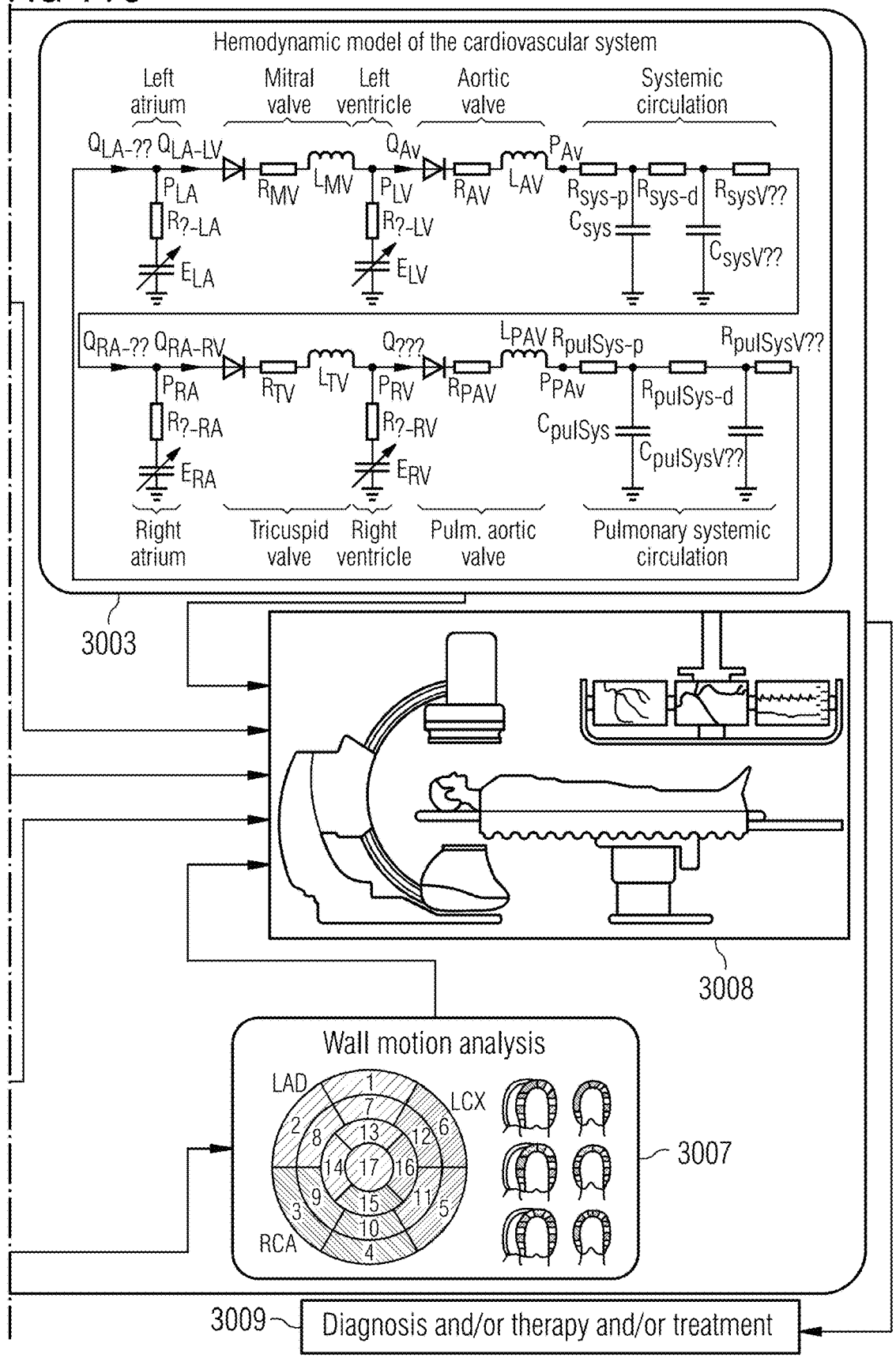

FIG. 11, a combination of FIGS. 11A-C, illustrates aspects in connection with a clinical workflow for cardiac function assessment.

At 3001, one or more input datasets are acquired. In the illustrated example, a first input dataset pertains to echocardiography data under rest conditions and a second input dataset pertains to echocardiography data under stress conditions. A respective measurement equipment 71 can be operated.

Further, a third input dataset includes context data and is obtained at 3002. The third input dataset could be loaded from a HIS. As a general rule, such context data can pertain to patient demographics, clinical history, routine measurements, e.g., blood test, cuff-based blood pressure, heart rate, et cetera.

Then, these input datasets are fed to the multi-level processing algorithm 110 and, at 3003, a respective algorithm—e.g., a NN or an empirically-parametrized model—is executed to obtain one or more hemodynamic measures of the whole-body hemodynamics circulation.

At 3004, perspective classification of the views of the echocardiography obtained at 3001 is performed using a respective NN, e.g., the NN 211 (cf. FIG. 10).

At 3005, the cardiac phases of the various frames of the movie data of the input datasets obtained at 3001 are determined, e.g., using the NN 212 (cf. FIG. 10).

At 3006, classification of geometrical properties of the cardiovascular system, e.g., of the LV is performed. This can include segmentation and linear/volumetric measurements.

At 3007, a wall motion analysis is performed. This could be based on using the NN 214 (cf. FIG. 10). A WMI can be output. The used NN can be configured depending on a stage and/or type of the encountered CVD. I.e., different WMI categories may be relied upon depending on the stage and/or type.

Then, at 3008, the outputs as obtained from 3003-3007 are all input to a consolidation-task NN 215 and the corresponding indication of the fitness of the cardiovascular system is thereby obtained.

This facilitates the decision on the functional significance of CAD, e.g., a requirement for revascularisation, at 3009.

Above, various examples have been described in the context of using multiple input datasets that can be associated with different imaging modalities. Alternatively or additionally to such scenarios, it is possible to process multiple input datasets that are associated with different stages of a CVD. This is illustrated in connection with FIG. 12.

Figure 12:
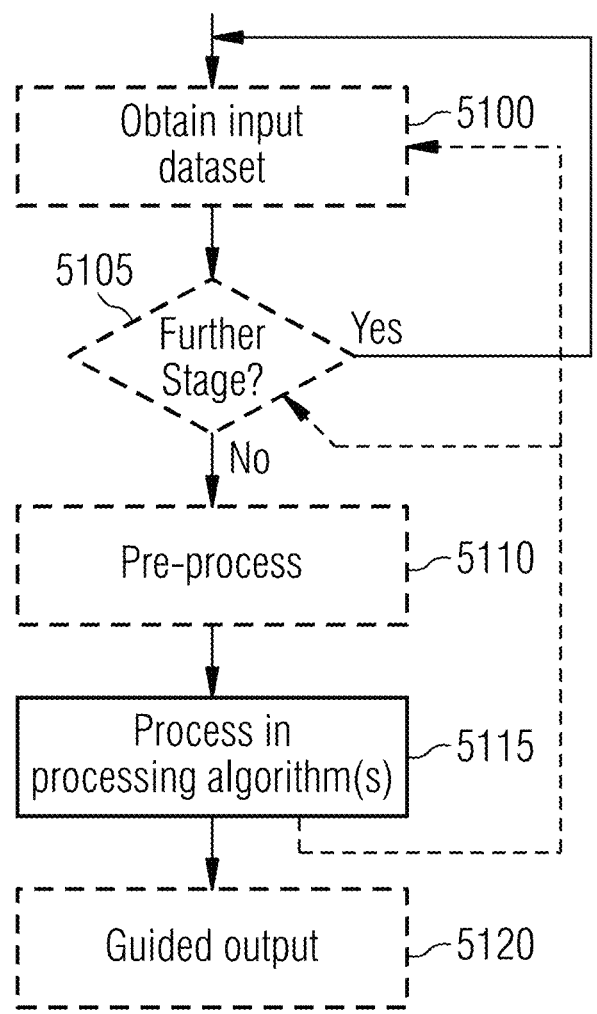
FIG. 12 is a flowchart of a method according to various examples.

FIG. 12 is a flowchart of a method according to various examples. For instance, the method of FIG. 12 could be executed by the server 80. For example, the method of FIG. 12 could be executed by the processing circuitry 81 of the server 80, upon loading program code from the memory 82.

FIG. 12 facilitates determining a trend of a fitness of the cardiovascular system. This is based on multiple input datasets associated with multiple stages of the associated CVD of the cardiovascular system.

At box 5100, an input dataset is obtained. This can include an acquisition: such acquisition can include providing control instructions to any one of the measurement equipment 71-73 (cf. FIG. 1). For instance, when acquiring an input dataset using an echocardiography equipment 71, this can include acquiring multiple frames 57 of a respective time series of frames, thereby forming the input dataset 51 (cf. FIG. 3). The input dataset obtained at box 5100 is associated with a certain stage of the CVD.

At optional box 5105, it is checked whether a further input dataset associated with a further stage of the CVD is required.

If a further input dataset is required, then box 5100 is re-executed, and the further input dataset is obtained, the further input dataset being associated with a further stage of the CVD.

For instance, these different stages can correspond to multiple subsequent visits of a patient to a radiologist.

The input datasets obtained at multiple iterations of box 5100 can pertain to the same or different imaging modalities and/or types. For example, it would be possible to rely on different types of input datasets for the different stages of the CVD. For illustration, it would be possible that for some stages of the CVD input datasets associated with a first imaging modality are available, while for another stage of the CVD, input datasets associated with a different, second imaging modality are available. Yet for a further stage of the CVD, it would be possible that a medical report associated with the CVD is available which includes a written description of one or more diagnostic metrics of the CVD. Such techniques have been illustrated above in connection with FIG. 5.

Once all input datasets have been obtained, the method commences to box 5110, where preprocessing of the input datasets is applied. For example, preprocessing as explained above in connection with FIG. 7 or FIG. 8 can be applied.

The preprocessing can facilitate extracting one or more diagnostic metrics from a medical report. This can include natural language processing. To give an example, above, techniques have been described in which a WMI can be determined using the NN 213 and the NN 214. It would be possible that the medical report specifies, in text form, the WMI and that it would be possible to extract the WMI from the medical report. Another example would pertain to one or properties of the cardiac system, e.g., linear measurements, volumetric measurements, LV mass, etc.

Alternatively or additionally, as part of the preprocessing at box 5110, it would be possible to determine a quality of data of the input datasets acquired at box 5100. Here, it would be possible to estimate a quality index for each one of the multiple input datasets, e.g., based on a predefined quality metric. The predefined quality metric can specify one or more characteristics to be checked in order to determine the quality index. For instance, the quality metric can specify an expected noise floor, types or number of artifacts, etc.

Such quality index can be used in various manners. For instance, filtering could be implemented at box 5110 to discard such data that has a low quality index. It would also be possible to determine a confidence level of the trend of the fitness based on such quality index. For example, the quality of a certain image in a given input dataset is deemed to be low by such a preprocessing algorithm, then, the evidence from that image could be downgraded when processing the multiple input datasets at box 5115.

Respective quality indices could also be output via a human-machine-interface 75 to an expert 62, to thereby describe a context and/or reliability of the trend of the fitness of the cardiovascular system.

For example, it would be possible that—based on such quality indices—a request for additional measurements to complement the multiple input datasets acquired at multiple iterations of box 5100 is output via the human machine interface 75. It would also be possible to provide the request to the control engine of a measurement equipment 71-73 to automate the acquisition.

Alternatively or additionally to such determining of the quality of the input datasets, the preprocessing at box 5110 could include one or more of the following techniques:

automated view classification with respect to perspectives; automated identification of clips; automated measurements; and/or automated assessment of global and regional cardiac motion.

For illustration, it would be possible to determine one or more perspectives of views included in imaging data of the multiple input datasets. For example, techniques as described above in connection with the NN 211 could be employed.

Alternatively or additionally, one or more clip snippets or—more—generally subsets of data—of the imaging dataset could be identified. Typically, each input dataset including imaging data includes a clip including multiple frames. It would be possible to extract one or more clip snippets from the clip, each clip only including a sub-fraction of all frames. The sub-fraction of frames can be best suited for a comparison with other sub-fractions of frames extracted from other input datasets. For instance, such subsets of data may be extracted that include matching content, e.g., same perspectives of views, similar cardiac phases, etc. This helps to compare frames having corresponding information content. More generally, the trend of the fitness of the cardiovascular system can then be determined based on such subsets of data having matching information content regarding the cardiovascular system.

As a general rule, there are various options available for determining whether subsets of data include matching content. In one example, it would be possible to compare classifications as obtained with other algorithms pertaining to, e.g., view classification, classification of the cardiac phases, etc. with respect to each other. Alternatively or additionally, it would be possible to use an auto-encoder neural network including an encoder and a decoder. Here, it would be possible to compare an encoded representation of a first subset with an encoded representation of a second subset and, if the encoded representations—e.g., resembling something like a checksum—correspond to each other, then it can be assumed that the subsets include matching data. This can be repeated for different selections of the subset until the difference between the encoded representations is minimized.

Alternatively or additionally, it would be possible to classify one or more properties of the cardiovascular system, e.g., of the LV. For instance, it would be possible to make linear or volumetric measurements or apply segmentations to the image data included in the input datasets. Respective techniques as discussed above in connection with the artificial NN 213 (cf. FIG. 10) could be applied. Further example automated measurements include strain or biplane ejection fraction.

Global and/or regional cardiac motion could be assessed. Techniques with respect to a wall motion analysis as explained above in connection with the NN 214 could be applied.

An explanation of reasoning, e.g., a change of a quantification parameter and/or a qualitative analysis can be performed.

Next, at box 5115, the multiple input datasets—possibly subject to the preprocessing of box 5110—are processed at box 5115 using one or more processing algorithms. For example, one or more ML algorithm can be used. The ML algorithm can accept a sequence of inputs associated with the multiple input datasets that are acquired at different stages of the CVD. Meta-information—e.g., the quality index and/or the view classification—as obtained from box 5110 can be received as a further input. The ML algorithm can implement a comparison between those sequences of inputs, to obtain a trend of the fitness of the cardiovascular system across the multiple stages of the disease.

Figure 16:
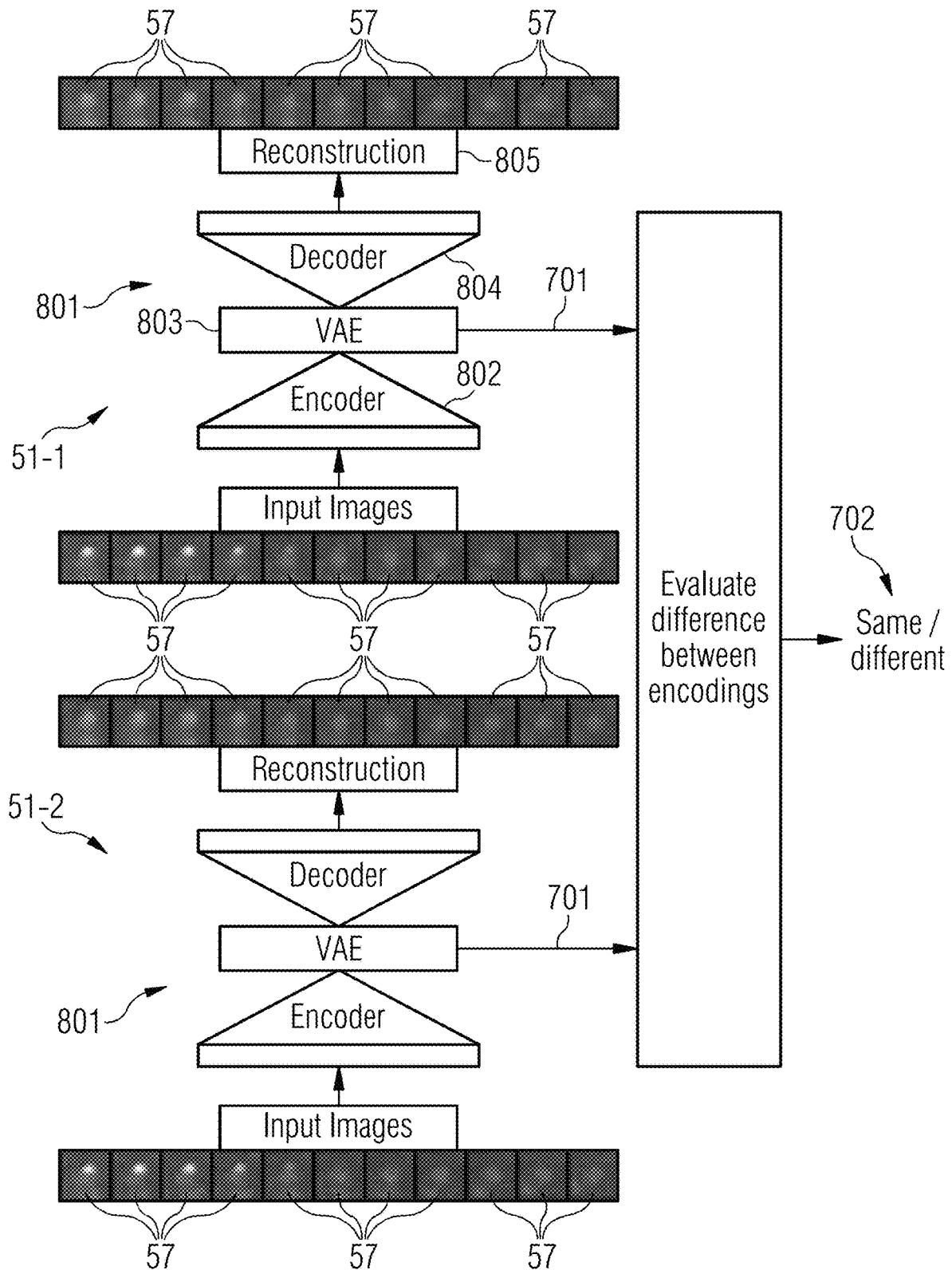
FIG. 16 schematically illustrates a multi-level processing algorithms according to various examples.

As a general rule, various options are available for implementing the one or more processing algorithms, e.g., ML algorithms, at box 5115. In one example, a multi-level processing algorithm 110 as explained in connection with FIG. 9 could be used. Another example (explained in connection with FIG. 16) may rely on a deep NN to automatically detect a change in cardiac function in echocardiographic images. The deep NN may implement an auto-encoder architecture 801. Here, the auto-encoder architecture includes an encoder NN 802. The encoder NN is configured to determine an encoded representation 803 of one or frames 57 (e.g., a clip snippet appropriately selected in the preprocessing of box 5110) of an echocardiographic movie. The decoder NN 804 is configured to decode the encoded representation, so as to yield a decoded representation 805 of the echocardiographic movie. Unsupervised training can be used so as to minimize a difference between the input and the output of the auto encoder architecture. The auto-encoder architecture is trained to reproduce the input frame or frames.

Optionally, additional output tasks may be defined, which assess the cardiac function, i.e., determine the fitness 701 of the cardiovascular system. Defining such additional task may help in obtaining an embedding that is highly relevant for the cardiac function assessment.

In particular, it would be possible to determine whether a respective indicator is indicative of the fitness of the cardiovascular system based on the encoded representation 803—reducing dimensionality—of the one or more input frames. Then, it would be possible to make a comparison between such indicators indicative of the fitness, so as to obtain the trend 702.

This approach may be used both to analyze the change in cardiac function (as described above) and to find matching pairs of images between different studies. Specifically, a cascaded approach may be employed, where first the matching pairs of frames 57 are found—e.g., at box 5510 of FIG. 12—and then the change in cardiac function is evaluated.

Next, —and referring again to FIG. 12—at optional box 5120, a guided output of data included in the multiple input datasets can be provided to a user/medical practitioner, based on the trend of the fitness of the cardiovascular system across the multiple stages of the disease as determined at box 5115.

For instance, it would be possible that the at least one processing algorithm, at box 5115, selects a subset of data from the multiple input datasets based on the trend of the fitness of the cardiovascular system and then provides this subset of the data to the human machine interface for expert review.

Thereby, the display of relevant images such as clip snippets can be guided by the one or more processing algorithms of box 5115, thereby enabling an efficient review workflow. Instead of manually arranging the relevant clip snippets in each time point, each having up to 200 clips, it is possible to automatically select the relevant images or frames for comparison at each stage of the disease. For illustration, it would be possible that the at least one processing algorithm box 5115 is configured to provide a classification of frames of time-series data included in the input dataset with respect to depicted content. For example, this could relate to a classification of geometrical properties of the cardiovascular system, anatomic features, or perspective of the views. Respective techniques have been explained above in connection with, e.g., FIG. 10. Then, it would be possible to select subsets of the data including a respective clip snippet of the time-series data so that they have similar classifications with respect to the depicted content.

Figure 13:
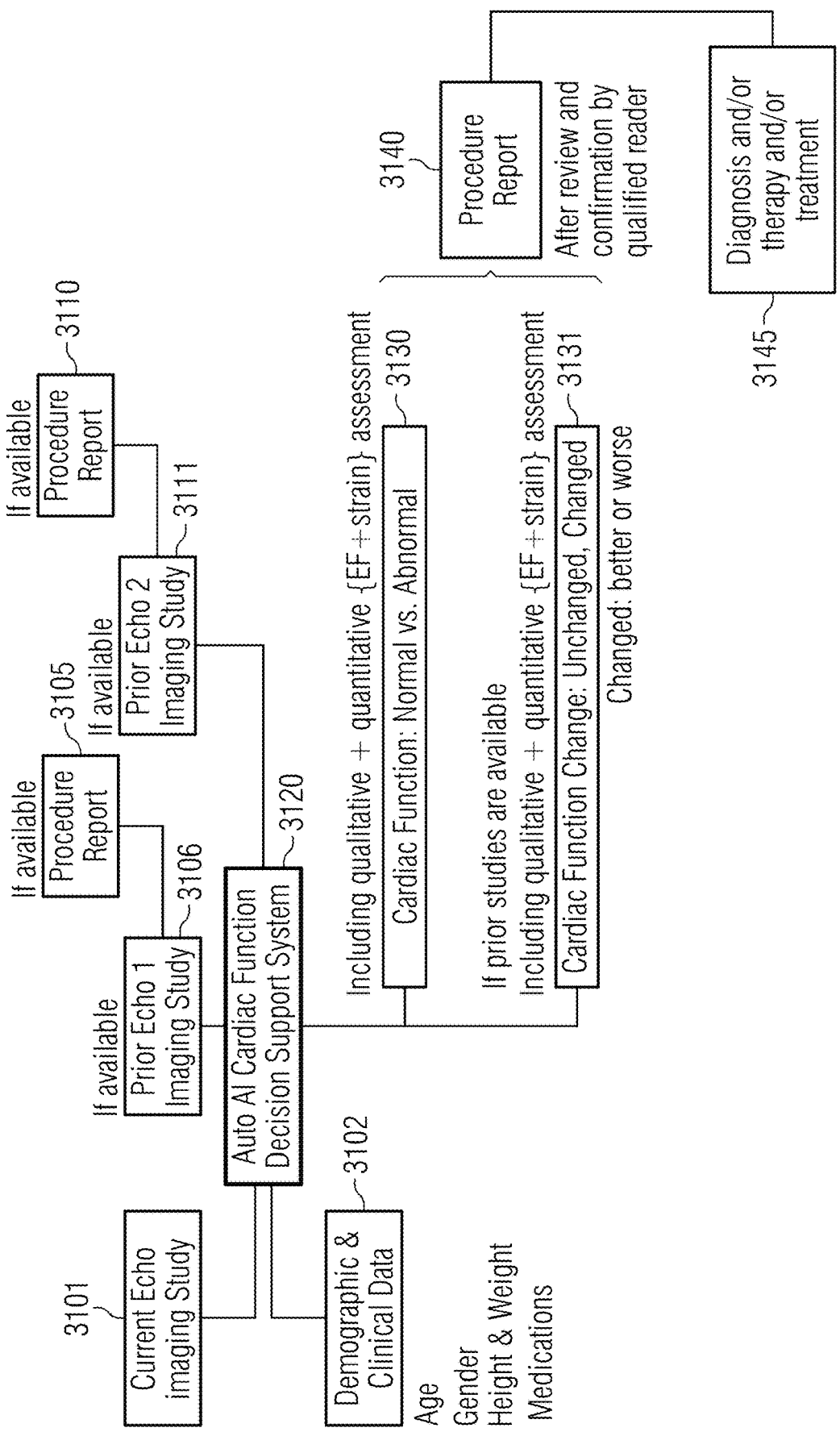
FIG. 13 schematically illustrates a processing algorithm according to various examples.

FIG. 13 illustrates a workflow for cardiac function assessment according to various examples. For example, the workflow according to FIG. 13 could be implemented by the method according to FIG. 12.

At box 3101, a current echocardiography imaging data is obtained as an input dataset.

At box 3102, and input dataset indicative of context data associated with the patient is obtained. This can pertain to demographics and/or clinical data such as age, gender, height, weight, and/or medications of the patient.

At box 3106, one or more input datasets associated with an earlier stage of the CVD are obtained. This can include obtaining, at box 3105, and input dataset including a medical report of a practitioner drawn up in connection with imaging data and/or other medical measurements taken at that earlier stage of the CVD. The one or more input datasets obtained at box 3106 can also include imaging data, e.g., an earlier echocardiography imaging data.

Similarly, at box 3111, one or more input datasets associated with yet another earlier stage of the CVD are obtained. This can, again, include obtaining, at box 3110, an input dataset including a medical report of a practitioner drawn up in connection with imaging data and/or other medical measurements taken at that yet another earlier stage of the CVD. The one or more input datasets obtained at box 3111 can also include imaging data, e.g., an earlier echocardiography imaging data.

At box 3120, one or more processing algorithms are executed. This can pertain to executing one or more pre-processing algorithms (cf. FIG. 12, box 5110), and/or executing one or more processing algorithms (cf. FIG. 12, box 5115). ML algorithms may be employed, e.g., NNs.

Then, at box 3130, an indicator indicative of the fitness of the cardiovascular system is output. As illustrated, the fitness can be associated with a classification into normal versus abnormal.

At box 3131, a trend of the fitness is output, e.g., here classified as unchanged and changed.

At box 3140, it would be possible to generate a procedure report, e.g., based on a guided output as discussed in connection with FIG. 12: box 5120.

At box 3145, it would be possible to follow up based on the procedure report of box 3140 or the fitness indication obtained at box 3130 and/or box 3131 with a diagnosis and/or therapy and/or treatment.

Above, techniques have been described in connection with inference of the fitness of the cardiovascular system based on one or more input datasets. This has been described, amongst other, in connection with the workflows of FIG. 11 and FIG. 13. Such techniques can employ ML algorithms. These ML algorithms can be parameterized by a training process. Aspects with respect to the training process are described in connection with FIG. 14.

Figure 14:
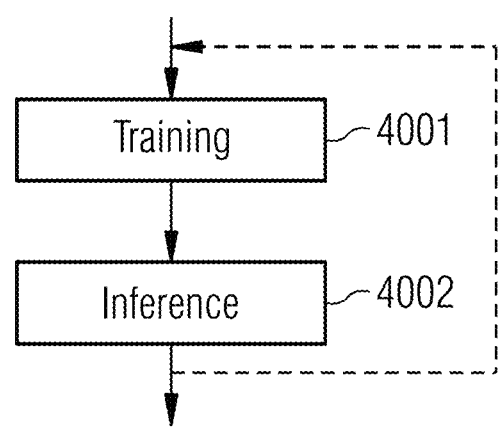
FIG. 14 is a flowchart of a method according to various examples.

FIG. 14 is a flowchart of a method according to various examples. The method of FIG. 14 illustrates aspects in connection with training of an ML algorithm and inference based on the trained ML algorithm, according to various examples. For instance, ML algorithms as described above in connection with FIG. 6 and/or FIG. 12 can be trained using techniques as described in connection with FIG. 14.

The ML algorithm is trained at box 4001. Then, based on the trained ML algorithm, one or more values can be inferred, at box 5002.

As illustrated in FIG. 14, training at box 4001 can precede the inference at box 4002. For example, to avoid a cold-start problem, it would be possible to start with supervised learning using specific training input datasets.

As a general rule, different configurations may be trained for different stages and/or types of the CVD. For instance, it would be possible to discriminate between a first configuration for a stable CAD and a second configuration for an acute CAD. Different parameter sets can be trained. In such a scenario, it would be possible to select between these configurations depending on a current state of the disease.

In some examples, based on outputs obtained from the inference at box 4002, training can be re-executed; this is illustrated by the dashed arrow in FIG. 14. This can refine the parametrization of the ML algorithms and increase its accuracy. In particular, semi-supervised or unsupervised techniques using labeling functions can be employed.

Labeling functions generally define a ruleset to generate ground truth for input datasets. Labeling functions can receive an input and derive one or more labels for the input datasets. Then, during the training, it is possible to compare an output of the ML algorithm with the one or more labels and minimize the corresponding difference, e.g., by an iterative optimization minimizing a loss function correspondingly defined. Labeling functions can be defined in the context of data programming framework, see Ratner, Alexander J., et al. "Data programming: Creating large training sets, quickly." Advances in neural information processing systems. 2016. In such a framework, multiple labeling functions can be provided that have inter-dependencies on each other.

The labeling functions can be used in connection with multi-task learning techniques. More specifically, based on the labeling functions, a coherent training of the multiple NNs of the multi-task level 112 can be implemented. This can be, in particular, helpful for a scenario in which multiple labeling functions are used to create ground-truth for different NNs of the multi-task level, the multiple labeling functions having interdependencies. Interdependencies can relate to a scenario in which the output of a given labeling function depends on the output of one or more further labeling functions and/or an intermediate state of one or more further labeling functions.

Various techniques in connection with training based on labeling functions are based on the finding that noisy training labels may be exploited by specifically encoding the weak supervision in the form of labeling functions. Labeling functions may have a widely varying error rate and may conflict on certain data points. They can be modelled as a generative process, leading to an automated denoising by learning the accuracies of the labeling functions along with the correlation structure. Further, various multi-task learning techniques can be employed, addressing both hard and soft parameter sharing and addressing aspects like uncertainty based loss weighting, learning rate tuning, and employing the predictions as estimates. The labeling function need not have perfect accuracy or recall; rather, it represents the pattern that the user wishes to impart their model and that is easier to encode as a labeling function then as a set of hand-labelled examples. Labeling function can be based on external knowledge bases, libraries or ontologies, can express heuristic patterns, or relate to some hybrid of these types. The use of labeling functions is also strictly more general than manual annotations, as a manual annotation can always be directly encoded by a labeling function. Importantly, labeling functions can overlap conflict and even have dependencies which users can provide as part of data programming specifications.

Since cardiac function assessment can be a complex task, depending on a large set of individual measurements and assessments collected as input datasets, it is likely that some datasets are incomplete, e.g. a certain type of image or measurements is missing. Alternatively, some images may have a too low image quality to be useful in the analysis. In this context, the data programming approach described herein still allows for the usage and exploitation of such datasets since missing labels/measurements are allowed. Furthermore, the data programming approach also allows for an efficient combination of manual and automated annotations, for the same or different sub-tasks Multitask learning is the key to allowing the system to identify the features in the input data that contain the information best explaining the clustering of data in use by the labeling process.

In the illustrated examples, multiple labeling functions may be defined to operate based on data obtained in the follow-up clinical workflow based on the input datasets used to determine the fitness of the cardiovascular system. For example, the labeling functions may obtain information from 3009 and/or 3145 (cf. FIG. 11 and FIG. 13). The labeling functions may obtain one or more of the following as input: invasively measured fractional flow reserve; clinical decision; patient outcome, e.g., based on follow-up information; stenosis grade, e.g., is determined by analyzing the coronary angiography, e.g., transformed to a binary label by employing a threshold; wall motion score index, e.g., transformed to a binary label by employing a threshold, as determined by an expert. Then, one or more of the NNS 211-214 of the multi-task level 112 and/or the NN 215 of the consolidation-task level 113 can be trained based on labels obtained from the one or more labeling functions.

A few example labeling functions are summarized in TAB. 1 below:

TABLE 1

Examples of labeling functions for training

| | |
|---|---|
| For indicator indicative of clinical decision on coronary revascularization (i.e., fitness = "revascularization" or "revascularization") | invasively measured FFR: GT = FFR <= 0.8 (or 0.75) |
| | clinical decision: GT = was the patient sent to the cathlab or not |
| | patient outcome: GT = did the patient have a MACE (major adverse cardiac event) within the following x years/months? Was the patient rehospitalized within the following x years/months |
| | stenosis grade (as determined by analyzing the coronary angiographies): GT = stenosis grade >= 50% (or 70%) |
| | wall motion score index, transformed to a binary label by employing a threshold: GT = wall motion score index >= threshold value |
| Labeling functions for view classification: | manual annotation |

TABLE 1-continued

Examples of labeling functions for training

| | |
|---|---|
| Labeling functions for cardiac phase: | prediction performed by another model (deep learning or image processing based) manual annotations |
| | derived by processing a simultaneously acquired ECG signal (typically ECG is indeed recorded during an echocardiography exam) |

Some of those values of the labeling functions are typically not available for all patients. I.e., input to the labeling functions may be sparse. One of the advantages of the above-defined approach is that for each labeling function one can also assign and 'abstain' value. For example, for the labeling function defined based on the patient outcome, it may either have a positive level (in case the patient has had a major adverse cardiovascular event, or an 'abstain' labeling case the follow-up period is not very large, and hence a definitive negative label cannot be assigned.

Summarizing, above techniques have been described which enable to determine the fitness of the cardiovascular system of a patient in an automated manner. Here, one or more ML algorithms can be employed. Multiple input datasets, e.g., using multiple imaging modalities and/or acquired at different stages of a CVD, can be used. Multi-task learning can be employed to improve the accuracy of the final output, by employing a multi-level algorithm that includes a multi-task level. Here, labeling functions can be used during the training to improve the accuracy of the ground truth labels. By combining labeling functions from multiple sources having some individual suboptimal accuracy, one can obtain higher quality ground truth labels. Denoising of the labels can be achieved.

Although the invention has been shown and described with respect to certain preferred embodiments, equivalents and modifications will occur to others skilled in the art upon the reading and understanding of the specification. The present invention includes all such equivalents and modifications and is limited only by the scope of the appended claims.

For illustration, various examples have been described above in connection with a CAT (cf. FIG. 10). Here, in particular, it is possible to determine the fitness 701 of the cardiovascular system in terms of revascularization being required or not being required. This, however, is an example only. Other examples are possible and one possible example is illustrated in connection with FIG. 15.

Figure 15:
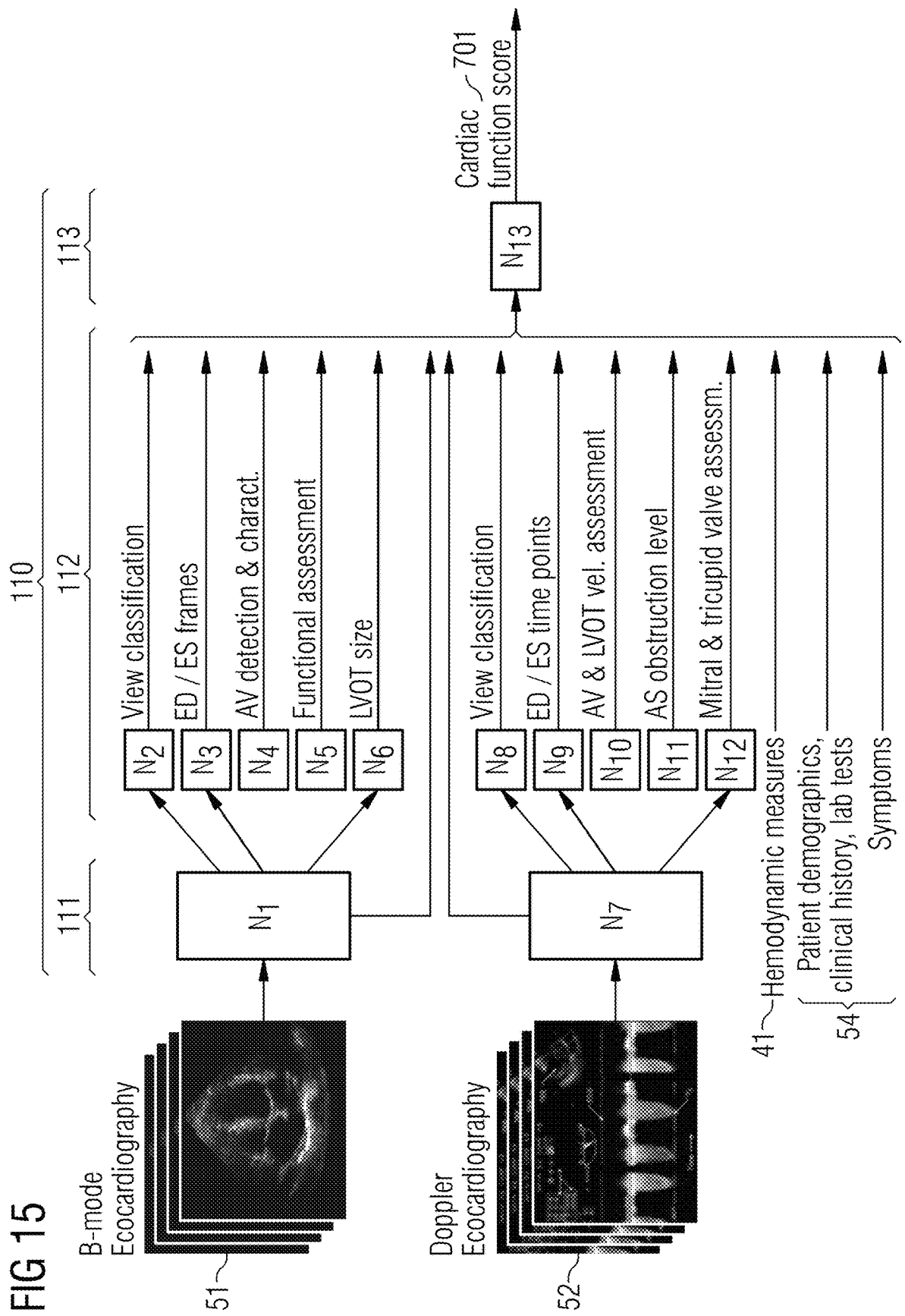
FIG. 15 schematically illustrates details of the multi-level processing algorithm of FIG. 9 according to various examples.

FIG. 15 schematically illustrates an example implementation of the multi-level processing algorithm 110 to determine a cardiac function score indicative of the fitness 701 of the cardiovascular system. FIG. 15 illustrates an example in the context of aortic valve stenosis as CVD. Both b-mode and Doppler echocardiographic imaging data is provided as input datasets 51, 52 to the multi-level processing algorithm, alongside non-imaging data such as hemodynamic measures 41 and context data in an input dataset 54.

The b-mode images will be first processed by a set of layers (noted N1) of the preprocessing level 111 which are common for all tasks. Next, sub-networks (N2-N6) of the multi-task level 112 are employed for different tasks, view classification, classification of cardiac phases, detecting and characterizing the valves, performing a functional cardiac assessment (ejection fraction, stroke volume, the LV mass index, etc.), LVOT diameter measurement. Similarly, the Doppler imaging data of the input dataset 52 are processed separately (N7-N12), to estimate diagnostic metrics such as view classification, classification of cardiac phases, determining the velocity through the LVOT and the valves, determining the level of flow obstruction, assessing the mitral and tricuspid valves. Finally, N13 of the consolidation level 113 computes the cardiac function score.

For further illustration, various techniques have been explained in connection with the left ventricle of the heart. Similarly, characteristics and properties of other heart chambers of the heart can be considered in the techniques described herein.

For still further illustration, various techniques have been described in the context of processing datasets at a server or locally at a medical measurement apparatus. As a general rule, all or some of the processing tasks described throughout this disclosure could also be implemented by cloud computing techniques. In this regard, it would be possible to rely on remote data centers, e.g., distanced from the respective medical facility at which medical data is acquired.

The invention claimed is:

1. A method, comprising:
processing at least one input dataset using a multi-level machine learning processing algorithm, one or more of the at least one input dataset comprising imaging data of a cardiovascular system of a patient,
wherein the multi-level processing algorithm comprises a multi-task level and a consolidation-task level, wherein an input of the consolidation-task level is coupled to an output of the multi-task level, wherein the multi-task level is configured to determine multiple diagnostic metrics of the cardiovascular system based on the at least one input dataset, wherein the consolidation-task level is configured to determine a fitness of the cardiovascular system of the patient,
wherein the multi-level processing algorithm further comprises a pre-processing level, the pre-processing level being configured to determine a quality index for each one of the at least one input dataset, the pre-processing level further configured to filter at least one of the at least one input dataset based on the quality index and/or determine a confidence level of the fitness based on the quality indexes.

2. The method of claim 1, wherein the multiple diagnostic metrics comprise a classification of perspectives of views of the imaging data.

3. The method of claim 1, wherein the multiple diagnostic metrics comprise a classification of cardiac phases the imaging data.

4. The method of claim 1, wherein the multiple diagnostic metrics comprise a classification of anatomic features imaged by the imaging data.

5. The method of claim 1, wherein the multiple diagnostic metrics comprise a classification of properties of a heart chamber of the heart of the cardiovascular system, wherein the properties are from the group comprising: linear measurements; area measurements; volumetric measurements; mass; cardiac deformation; and/or segmentation.

6. The method of claim 1, wherein the multiple diagnostic metrics comprise a classification of a wall motion of the left ventricle of the heart of the cardiovascular system.

7. The method of claim 1, wherein the multiple diagnostic metrics comprise a classification of hemodynamics of a whole-body hemodynamic circulation associated with the cardiovascular system.

8. The method of claim 1, wherein the consolidation-task level is configured to determine the fitness further based on a classification of hemodynamics of a whole-body hemodynamic circulation associated with the cardiovascular system.

9. The method of claim 1, wherein consolidation-task level is configured to determine the fitness of the cardiovascular system of the patient by classifying a wall motion of a left ventricle.

10. The method of claim 1, wherein the at least one input dataset comprises multiple input datasets acquired at multiple stages of a disease of the cardiovascular system, wherein the consolidation-task level is configured to determine a trend of the fitness across the multiple stages of the disease.

11. The method of claim 1, wherein the at least one input dataset comprises a medical report associated with the disease of the cardiovascular system, wherein the multi-level processing algorithm is configured to extract at least one of the multiple diagnostic metrics from the medical report.

12. The method of claim 1, further comprising:
selecting between a first configuration of the multi-level processing algorithm and a second configuration of the multi-level processing algorithm depending on at least one of a current stage or a type of a disease associated with the cardiovascular system.

13. The method of claim 1, further comprising:
training one or more neural networks of at least one of the multi-task level or the consolidation-task level based on the at least one input dataset and one or more labeling functions, the one or more labeling functions determining a ground truth for the at least one input dataset based on one or more of the following inputs to the one or more labeling functions from the group of: a fractional flow reserve measurement; a clinical decision; a patient outcome; a stenosis grade determined based on a coronary angiography; and a wall motion score index.

14. A method, comprising:
processing, using at least one machine-learning processing algorithm, multiple input datasets indicative of at least one of measurements on a cardiovascular system of a patient or diagnostic metrics of the cardiovascular system, the multiple input datasets being associated with different stages of a disease of the cardiovascular system,
wherein the at least one processing algorithm is configured to determine a trend of a fitness of the cardiovascular system across the multiple stages of the disease of the cardiovascular system,
wherein the at least one processing algorithm is configured to select a subset of data from the multiple input datasets based on the trend of the fitness and to provide the subset of data to a human-machine-interface for expert review.

15. The method of claim 14, wherein one or more of the multiple input datasets comprise a medical report associated with the disease of the cardiovascular system, wherein the method further comprises:
pre-processing the one or more of the multiple input datasets comprising the medical report to extract associated one or more diagnostic metrics of the disease of cardiovascular system.

16. The method of claim 14, further comprising:
determining a quality index for one or more of the multiple input datasets, and based on the quality index, filtering one or more of the multiple input datasets prior to processing the multiple input datasets using the at least one processing algorithm.

17. The method of claim 14, further comprising:
determining a quality index for one or more of the multiple input datasets, wherein the at least one processing algorithm is configured to determine a confidence level of the trend of the fitness based on the quality index.

18. The method of claim 14, further comprising:
determining a quality index for one or more of the multiple input datasets, wherein the at least one processing algorithm is configured to provide, based on the quality index and to at least one of the human-machine-interface or a control engine of a measurement apparatus, a request for an additional measurement to complement the multiple input datasets.

19. The method of claim 14, wherein the at least one processing algorithm is an auto-encoder neural network, wherein the trend of the fitness is determined based on a comparison between encoded representations of pairs of the input dataset obtained from an encoder of the auto-encoder neural network.

20. The method of claim 14, further comprising:
selecting, from each one of the multiple input datasets, a subset of data, wherein the subsets of data of the multiple input datasets are compared with each other by the at least one processing algorithm.

21. A method of training one or more neural networks, the method comprising:

configuring a multi-level processing algorithm comprising a multi-task level and a consolidation-task level to determine a fitness of the cardiovascular system of the patient based on at least one input dataset comprising medical measurements of the cardiovascular system, wherein an input of the consolidation-task level is coupled to an output of the multi-task level, wherein the multi-task level is configured to determine multiple diagnostic metrics of the cardiovascular system based on the at least one input dataset, wherein the consolidation-task level is configured to determine the fitness of the cardiovascular system of the patient; and training the one or more neural networks based on the at least one input dataset and one or more labeling functions, the one or more labeling functions determining a ground truth for the at least one input dataset based on one or more of the following inputs to the one or more labeling functions from the group of: a fractional flow reserve measurement; a clinical decision; a patient outcome; a stenosis grade determined based on a coronary angiography; and a wall motion score index one or more characteristics of a subsequent clinical procedure of treatment of the cardiovascular system.

22. The method of claim 21, wherein multiple neural networks of the multi-task level are trained using multiple labeling functions, the multiple labeling functions having inter-dependencies.

\* \* \* \* \*